(12) United States Patent
Watanabe et al.

(10) Patent No.: US 8,562,814 B2
(45) Date of Patent: Oct. 22, 2013

(54) MEASUREMENT DEVICE AND SENSOR EJECTION METHOD

(75) Inventors: Hidenori Watanabe, Ehime (JP);
Toshiaki Iio, Ehime (JP)

(73) Assignee: Panasonic Corporation, Osaka (JP)

( * ) Notice: Subject to any disclaimer, the term of this patent is extended or adjusted under 35 U.S.C. 154(b) by 1126 days.

(21) Appl. No.: 12/376,267

(22) PCT Filed: Aug. 3, 2007

(86) PCT No.: PCT/JP2007/065246
§ 371 (c)(1),
(2), (4) Date: Feb. 3, 2009

(87) PCT Pub. No.: WO2008/016137
PCT Pub. Date: Feb. 7, 2008

(65) Prior Publication Data
US 2010/0012530 A1 Jan. 21, 2010

(30) Foreign Application Priority Data
Aug. 3, 2006 (JP) .................................. 2006-212485

(51) Int. Cl.
*G01N 27/327* (2006.01)
(52) U.S. Cl.
USPC .... 205/792; 422/82.01; 422/68.1; 435/287.1; 600/347; 204/403.01
(58) Field of Classification Search
USPC ............ 204/400–403.15; 422/401, 63, 82.05, 422/400, 402, 430, 68.1, 82.01; 600/583, 600/584, 309–367; 205/775, 777.5, 778, 205/792; 435/287.1
See application file for complete search history.

(56) References Cited

U.S. PATENT DOCUMENTS

2004/0020771 A1  2/2004  Taniike et al.
2006/0133956 A1* 6/2006  Hamanaka .................. 422/68.1

FOREIGN PATENT DOCUMENTS

JP   2003-114213   4/2003
JP   2004-4057     1/2004
JP   2004-61209    2/2004

OTHER PUBLICATIONS

International Search Report issued Nov. 6, 2007 in the International (PCT) Application No. PCT/JP2007/065246.
Written Opinion of the ISA issued Nov. 6, 2007 in the International (PCT) Application No. PCT/JP2007/065246.

* cited by examiner

*Primary Examiner* — J. Christopher Ball
*Assistant Examiner* — Jennifer Dieterle
(74) *Attorney, Agent, or Firm* — Wenderoth, Lind & Ponack, L.L.P.

(57) ABSTRACT

A measurement device includes a sensor holding part (10) which detachably holds a sensor having an electrode terminal at its one end, a connection terminal (14) which elastically contacts the electrode terminal of the sensor to take out a signal required for analysis, an ejection mechanism having a pushing member (11) which is extrudably attached to the device body, and pushes the sensor that is held by the sensor holding part (10) with the electrode terminal thereof elastically contacting the connection terminal (14) while releasing the contact between the sensor electrode terminal and the connection terminal (14), thereby to eject the sensor from the sensor holding part (10), and a first brake part (13) which elastically contacts the sensor to brake the movement of the sensor in the ejection direction while performing the extrusion operation of pushing out the sensor by the ejection mechanism.

29 Claims, 15 Drawing Sheets

MEASUREMENT DEVICE AND SENSOR EJECTION METHOD

TECHNICAL FIELD

The present invention relates to a measurement device for collecting and measuring a sample such as body fluid, and more particularly, to an ejection mechanism for ejecting a sensor from the measurement device.

BACKGROUND ART

Conventionally, a measurement device and sensor for electrochemically measuring blood glucose level has been put to practical use as an analysis device for easily analyzing the characteristics of body fluid.

As shown in FIG. 15, there is disclosed a measurement device 700 including an ejection lever 2 which is provided slidably to a measurement device body 1, and a slider (not shown) which moves in response to the ejection lever 2 to push out a sensor 200 (refer to Patent Document 1). The sensor 200 has a cavity (not shown) for collecting blood at its front end as shown in FIG. 17(a). An electrode and a reagent layer containing such as an enzyme and an electron carrier are provided in the cavity. Further, an electrode terminal 200a is provided at a rear end of the sensor 200.

The measurement device 700 has an electric circuit which applies a voltage to the electrode of the sensor 200 to measure a current value according to the glucose concentration in blood, which current is generated by a reaction between glucose in blood and the reagent layer, and the measurement device 700 calculates a blood glucose level according to the measured current value and displays the blood glucose level on a display 700a.

FIG. 16(a) is an exploded perspective view of the conventional measurement device 700.

With reference to FIG. 16(a), in the measurement device 700, two claws 2a of the ejection lever 2 are inserted in a rectangle hole 1a of the measurement device body 1, whereby the ejection lever 2 is slidably attached to the measurement device body 1. The ejection lever 2 has a plastic spring 2b.

A base plate 5 having a connector 16 is screwed to the measurement device body 1. The connector 16 has a pushing member 11. The pushing member 11 is fitted to a slider fitting part 2c of the ejection lever 2 through a notch 5a of the base plate 5 and a notch of the connector 16. Accordingly, the pushing member 11 is slidable along the longitudinal direction of the notch 5a in response to the ejection lever 2.

Hereinafter, the operation of ejecting the sensor 200 will be described with reference to FIG. 16(b). FIG. 16(b) is a cross-sectional view of the measurement device 700 in the state where the measurement device body 1, the ejection lever 2, and the base plate 5 shown in FIG. 16(a) are combined, wherein the long and thin sensor chip 200 for collecting blood is set in the measurement device 700.

In order to eject the sensor 200 after the sample such as body fluid is measured with the sensor 200 attached to the measurement device 700, initially, the ejection lever 2 is slid with a finger along the direction of an arrow shown in FIG. 16(b). Then, the pushing member 11 is also slid along the arrow direction in response to the ejection lever 2 and pushes the sensor 200 out of the connector 16, and thus the sensor 200 is ejected from the measurement device body 1.

Since the ejection lever 2 has the plastic spring 2b, when the sensor 200 is ejected by sliding the ejection lever 2, a force which urges the ejection lever 2 in the direction reverse to the sensor ejecting direction is generated by the plastic spring 2b.

Further, as shown in FIG. 19, several electrodes (connection terminal) 14 included in the connector 16 may be positioned so as not to contact with a projection portion 11a of the pushing member in the connector 16 when the projection portion 11a is slid.

When the sensor 200 is ejected from the measurement device 700 by the ejection mechanism 700, the measurement of the blood glucose level by the measurement device 700 is completed.

In the conventional measurement device as described above, the operator can discard the sensor without touching the sample attached to the sensor, thereby avoiding infection of disease or the like. Further, since the sensor can be ejected by sliding the ejection lever 2, ejection of the sensor is facilitated.

Patent Document: Japanese Published Patent Application No. 2003-114213

DISCLOSURE OF THE INVENTION

Problems to be Solved by the Invention

Using the conventional measurement device 700, the patient inserts the sensor 200 in the connector 701 of the measurement device 700 as shown in FIG. 17(b), and punctures his skin with a puncture device called a lancet device to perform a puncture operation for collecting body fluid, and then applies the collected body fluid to the sensor 200 to perform measurement. After the measurement is completed, the patient moves the ejection lever 2 which is slidably attached to the measurement device to push out the sensor 200 to which the body fluid is attached from the connector 701, thereby ejecting the sensor 200 from the measurement device body 1. Thereafter, the patient inserts a new sensor 200 to perform a measurement again. In this way, the operator such as a patient, or a helper for the patient, or a hospital worker must insert and eject the sensor 200 for every measurement.

By the way, in the conventional ejection mechanism as described above, as shown in FIG. 18(b) which is an enlarged view of FIG. 18(a) showing a cross-section of a main part of the measurement device 700, since the sensor 200 is generally thin and flat and the sensor 200 is ejected by the pushing member 11 with the electrode terminal 200a thereof being elastically pressed from above by the connection terminal 14, the sensor 200 is undesirably flicked out.

That is, when the sensor 200 is inserted, the connection terminal 14 is deformed so as to elastically press the electrode terminal 200a of the sensor 200 from above as shown in FIG. 18(b). However, at the moment when the connection between the electrode terminal 200a of the sensor 200 and the connection terminal 14 is released, the connection terminal 14 has a restoring force R1 to return to the shape before the connection as shown in FIG. 18(c), and the sensor 200 is flicked in the ejection direction by this restoring force R1. As the result, as shown in FIG. 15, the sensor on which the sample such as body fluid is applied is undesirably jumped out with an excessive speed V1 that is not intended by the operator, and the sample applied to the sensor 200 might be attached to the human body. There is a risk of an infection disease if the sample contains a disease agent. Therefore, a measurement device and a sensor ejection method which can safely discard the sensor have been demanded.

The present invention is made to solve the above-described problems and has for its object to provide a measurement device and a sensor ejection method, which can control the ejection speed when the sensor is ejected from the measurement device to prevent the sensor from being rapidly jumped out beyond necessity.

Measures to Solve the Problems

In order to solve the above-described problems, according to a first aspect of the present invention, there is provided a measurement device for electrochemically analyzing an analysis sample which is collected by a sensor having an electrode terminal at its one end, comprising: a sensor holding part which is integrated with the measurement device body, and detachably holds the sensor; a connection terminal which is elastic-deformably supported by the measurement device body, and elastically contacts the electrode terminal of the sensor that is held by the sensor holding part to take out a signal required for analysis; an ejection mechanism having an element which is extrudably attached to the measurement device body, the element being brought into contact with the front side surface of the sensor viewed from the measurement device side so as to push the sensor which is held by the sensor holding part with the electrode terminal thereof elastically contacting the connection terminal while releasing the elastic contact of the electrode terminal of the sensor with the connection terminal, thereby to eject the sensor from the sensor holding part; and a brake means provided at a portion of the measurement device body, the brake means elastically contacting the sensor to brake the movement of the sensor in the ejection direction while performing the operation of pushing the sensor by the ejection mechanism.

Thereby, the sensor can be prevented from jumping out more rapidly than necessary when it is ejected from the measurement device.

According to a second aspect of the present invention, in the measurement device defined in the first aspect, the ejection mechanism includes the brake means.

Thereby, the ejection mechanism and the brake means can be integrally formed, resulting in a reduction in the number of component parts.

According to a third aspect of the present invention, in the measurement device defined in the first aspect, the brake means comprises an elastic material.

Thereby, the movement speed of the sensor in the ejection direction can be reduced.

According to a fourth aspect of the present invention, in the measurement device defined in the third aspect, the elastic material is any of a plastic, a metal, and a rubber.

According to a fifth aspect of the present invention, in the measurement device defined in the first aspect, the brake means is a first brake part which is provided at a position that contacts a side surface or a plane surface of the sensor.

Thereby, the movement speed of the sensor in the ejection direction can be reduced, and further, the brake part can be simply configured without the necessity of complicating the configuration such that the sensor is brought into contact with the brake part only when ejecting the sensor. Furthermore, since the brake part contacts the side surface or one plane surface of the brake part, temperature variation caused by a frictional force or the like does not adversely affect the measurement result of the sample.

According to a sixth aspect of the present invention, in the measurement device defined in the first aspect, the brake means is a second brake part comprising a rotating body, which is provided at a position that contacts a side surface or a plane surface of the sensor.

Thereby, the movement speed of the sensor in the ejection direction can be reduced, and further, the brake part can be simply configured without the necessity of making the configuration complicated such that the brake part is brought into contact with the sensor only when ejecting the sensor.

According to a seventh aspect of the present invention, in the measurement device defined in the first aspect, the brake means contacts the sensor at a sensor position where the contact of the connection terminal to the electrode terminal of the sensor is released or at a sensor position which is by a predetermined amount anterior to the sensor position where the contact is released.

Thereby, since the brake means contacts the sensor after the connection terminal and the sensor electrode terminal are completely separated from each other, the movement speed of the sensor in the ejection direction can be reliably reduced regardless of the pressing force of the connection terminal to the sensor electrode terminal.

According to an eighth aspect of the present invention, in the measurement device defined in the fifth aspect, the first brake part contacts the sensor at a sensor position where the contact of the connection terminal to the electrode terminal of the sensor is released or at a sensor position which is by a predetermined amount anterior to the sensor position where the contact is released.

Thereby, since the first brake part contacts the sensor after the connection terminal and the sensor electrode terminal are completely separated from each other, the movement speed of the sensor in the ejection direction can be reliably reduced regardless of the pressing force of the connection terminal to the sensor electrode terminal.

According to a ninth aspect of the present invention, in the measurement device defined in the sixth aspect, the second brake part contacts the sensor at a sensor position where the contact of the connection terminal to the electrode terminal of the sensor is released or at a sensor position which is by a predetermined amount anterior to the sensor position where the contact is released.

Thereby, since the second brake part contacts the sensor after the connection terminal and the sensor electrode terminal are completely separated from each other, the movement speed of the sensor in the ejection direction can be reliably reduced regardless of the pressing force of the connection terminal to the sensor electrode terminal.

According to a tenth aspect of the present invention, in the measurement device defined in the first aspect, the brake means comprises a third brake part which contacts the sensor to brake the sensor by a solenoid when ejecting the sensor.

Thereby, it is possible to prevent the sensor from jumping out more rapidly than necessary when it is ejected from the measurement device.

According to an eleventh aspect of the present invention, in the measurement device defined in the tenth aspect, the third brake part comprises a position detection means for detecting the position of the ejection mechanism, a solenoid drive means for driving the solenoid according to an output of the position detection means, and a brake arm which is movable in conjunction with the solenoid.

Thereby, it is possible to prevent the sensor from jumping out more rapidly than necessary when it is ejected from the measurement device.

According to a twelfth aspect of the present invention, in the measurement device defined in the first aspect, the brake means comprises a fourth brake part which contacts the sensor to brake the sensor by an eccentric cam when ejecting the sensor.

Thereby, it is possible to prevent the sensor from jumping out more rapidly than necessary when it is ejected from the measurement device.

According to a thirteenth aspect of the present invention, in the measurement device defined in the twelfth aspect, the fourth brake part comprises a cam drive lever which is moved in conjunction with an ejection lever provided in the ejection mechanism, and the eccentric cam having an engagement part that can be engaged with an end of the cam drive lever and a convex portion that contacts the sensor, and being rotatable around a shaft.

Thereby, it is possible to prevent the sensor from jumping out more rapidly than necessary when it is ejected from the measurement device.

According to a fourteenth aspect of the present invention, in the measurement device defined in the thirteenth aspect, the convex portion of the eccentric cam comprises an elastic material.

Thereby, the movement speed of the sensor in the ejection direction can be reduced.

According to a fifteenth aspect of the present invention, in the measurement device defined in the fourteenth aspect, the elastic material is any of a plastic, a metal, and a rubber.

According to a sixteenth aspect of the present invention, there is provided a measurement device which electrochemically analyzes an analysis sample that is collected by a sensor having an electrode terminal at its one end, comprising: a sensor holding part which is integrated with the measurement device body, and detachably holds the sensor; a connection terminal which is elastic-deformably supported by the measurement device body, and elastically contacts the electrode terminal of the sensor that is held by the sensor holding part to take out a signal required for analysis; an ejection mechanism having an element which is extrudably attached to the measurement device body, the element being brought into contact with the front side surface of the sensor viewed from the measurement device side so as to push the sensor which is held by the sensor holding part with the electrode terminal thereof elastically contacting the connection terminal while releasing the elastic contact of the electrode terminal of the sensor with the connection terminal, thereby to eject the sensor from the sensor holding part; and a fifth brake part provided at a portion of the measurement device body, the fifth brake part performing suction or exhaust of air to the sensor through a vent hole provided on the device body side to brake the movement of the sensor in the ejection direction while performing the operation of pushing the sensor by the ejection mechanism.

Thereby, it is possible to prevent the sensor from jumping out more rapidly than necessary when it is ejected, and further, there occurs no attrition due to friction because air is used, and a stable brake force can be maintained.

According to a seventeenth aspect of the present invention, in the measurement device defined in the sixteenth aspect, the fifth brake part comprises a position detection means for detecting the position of the ejection mechanism, a pump drive means for driving a pump which can perform suction or exhaust of air according to an output of the position detection means, and a flow channel which is connected to the pump at one end, and connected to the vent hole at the other end, the vent hole being provided opposed to the plane surface of the sensor.

According to an eighteenth aspect of the present invention, in the measurement device defined in the sixteenth aspect, the vent hole is provided having an appropriate angle with respect to the plane surface of the sensor.

Thereby, the direction of air which functions as a brake when ejecting the sensor can be arbitrarily selected.

According to a nineteenth aspect of the present invention, in the measurement device defined in the sixteenth aspect, the vent hole is provided at the upper surface or lower surface of the sensor, or at the both surfaces.

According to a twentieth aspect of the present invention, in the measurement device defined in the sixteenth aspect, a plurality of the vent holes are provided.

Thereby, the ejection direction and ejection position of the sensor can be made more stable.

According to a twenty-first aspect of the present invention, in the measurement device defined in the sixteenth aspect, the fifth brake part controls the amount of air to be sucked or exhausted by performing depressurizing or pressurizing.

Thereby, the ejection direction and ejection position of the sensor can be made more stable.

According to a twenty-second aspect of the present invention, there is provided a sensor ejection method for ejecting the sensor from the measurement device defined in the first aspect, comprising: a first step of pushing the ejection mechanism of the measurement device; a second step of bringing the ejection mechanism in contact with the front side surface of the sensor viewed from the measurement device body side so as to push the sensor which is held by the sensor holding part of the measurement device with the electrode terminal thereof elastically contacting the connection terminal of the measurement device while releasing the elastic contact of the electrode terminal of the sensor with the connection terminal of the measurement device, thereby to eject the sensor from the sensor holding part of the measurement device; and a third step of bringing the brake means of the measurement device in elastic contact with the sensor to brake the movement of the sensor in the ejection direction while performing the operation of pushing the sensor by the ejection mechanism.

Thereby, it is possible to prevent the sensor from jumping out more rapidly than necessary when it is ejected.

According to a twenty-third aspect of the present invention, there is provided a sensor ejection method for ejecting the sensor from the measurement device defined in the fifth aspect, comprising: a first step of pushing the ejection mechanism of the measurement device; a second step of bringing the ejection mechanism in contact with the front side surface of the sensor viewed from the measurement device body side so as to push the sensor which is held by the sensor holding part of the measurement device with the electrode terminal thereof elastically contacting the connection terminal of the measurement device while releasing the elastic contact of the electrode terminal of the sensor with the connection terminal of the measurement device, thereby to eject the sensor from the sensor holding part of the measurement device; and a third step of bringing the first brake part of the measurement device in elastic contact with the side surface of the sensor to brake the movement of the sensor in the ejection direction while performing the operation of pushing the sensor by the ejection mechanism.

Thereby, it is possible to prevent the sensor from jumping out more rapidly than necessary when it is ejected.

According to a twenty-fourth aspect of the present invention, there is provided a sensor ejection method of ejecting the sensor from the measurement device defined in the sixth aspect, comprising: a first step of pushing the ejection mechanism of the measurement device; a second step of bringing the ejection mechanism in contact with the front side surface of the sensor viewed from the measurement device body side so as to push the sensor which is held by the sensor holding part of the measurement device with the electrode terminal thereof elastically contacting the connection terminal of the measurement device while releasing the elastic contact of the electrode terminal of the sensor with the connection terminal of the measurement device, thereby to eject the sensor from the sensor holding part of the measurement device; and a third step of bringing the second brake part of the measurement device in elastic contact with the upper and lower surfaces of the sensor and rotating the second brake part to brake the movement of the sensor in the ejection direction while performing the operation of pushing the sensor by the ejection mechanism.

Thereby, it is possible to prevent the sensor from jumping out more rapidly than necessary when it is ejected.

According to a twenty-fifth aspect of the present invention, there is provided a sensor ejection method for ejecting a sensor from the measurement device defined in the eleventh aspect, comprising: a first step of pushing the ejection mechanism of the measurement device; a second step of detecting the position of the ejection mechanism; a third step of driving the solenoid according to the position of the ejection mechanism; and a fourth step of driving the brake arm which is movable in conjunction with the solenoid to bring the third brake part of the measurement device in elastic contact with the sensor, thereby to brake the movement of the sensor in the ejection direction.

Thereby, it is possible to prevent the sensor from jumping out more rapidly than necessary when it is ejected.

According to a twenty-sixth aspect of the present invention, there is provided a sensor ejection method for ejecting a sensor from the measurement device defined in thirteenth aspect, comprising: a first step of pushing the ejection mechanism of the measurement device; a second step of driving the cam drive lever of the measurement device to bring it into contact with the eccentric cam; and a third step of rotating the eccentric cam around the shaft to bring the convex portion of the eccentric cam in elastic contact with the sensor, thereby to brake the movement of the sensor in the ejection direction.

Thereby, it is possible to prevent the sensor from jumping out more rapidly than necessary when it is ejected.

According to the twenty-seventh aspect of the present invention, there is provided a sensor ejection method for ejecting a sensor from the measurement device defined in the sixteenth aspect, comprising: a first step of pushing the ejection mechanism of the measurement device; a second step of detecting the position of the ejection mechanism; a third step of driving a pump according to the position of the ejection mechanism; and a fourth step of performing suction or exhaust of air through a vent hole provided in the measurement device body via a flow channel connected to the pump, thereby to brake the movement of the sensor in the ejection direction.

Thereby, it is possible to prevent the sensor from jumping out more rapidly than necessary when it is ejected.

Effects of the Invention

According to the measurement device of the present invention, since the sensor is ejected with a stable speed with the amount of jumping-out of the sensor from the measurement device being controlled when the sensor is being ejected, it is possible to prevent the sensor from being ejected with an excessive speed which cannot be expected by the operator, and thereby the operator such as a patient, or a helper for the patient, or a hospital worker can safely discard the sensor without directly touching the sensor to which the sample such as body fluid is attached.

Figure 1:
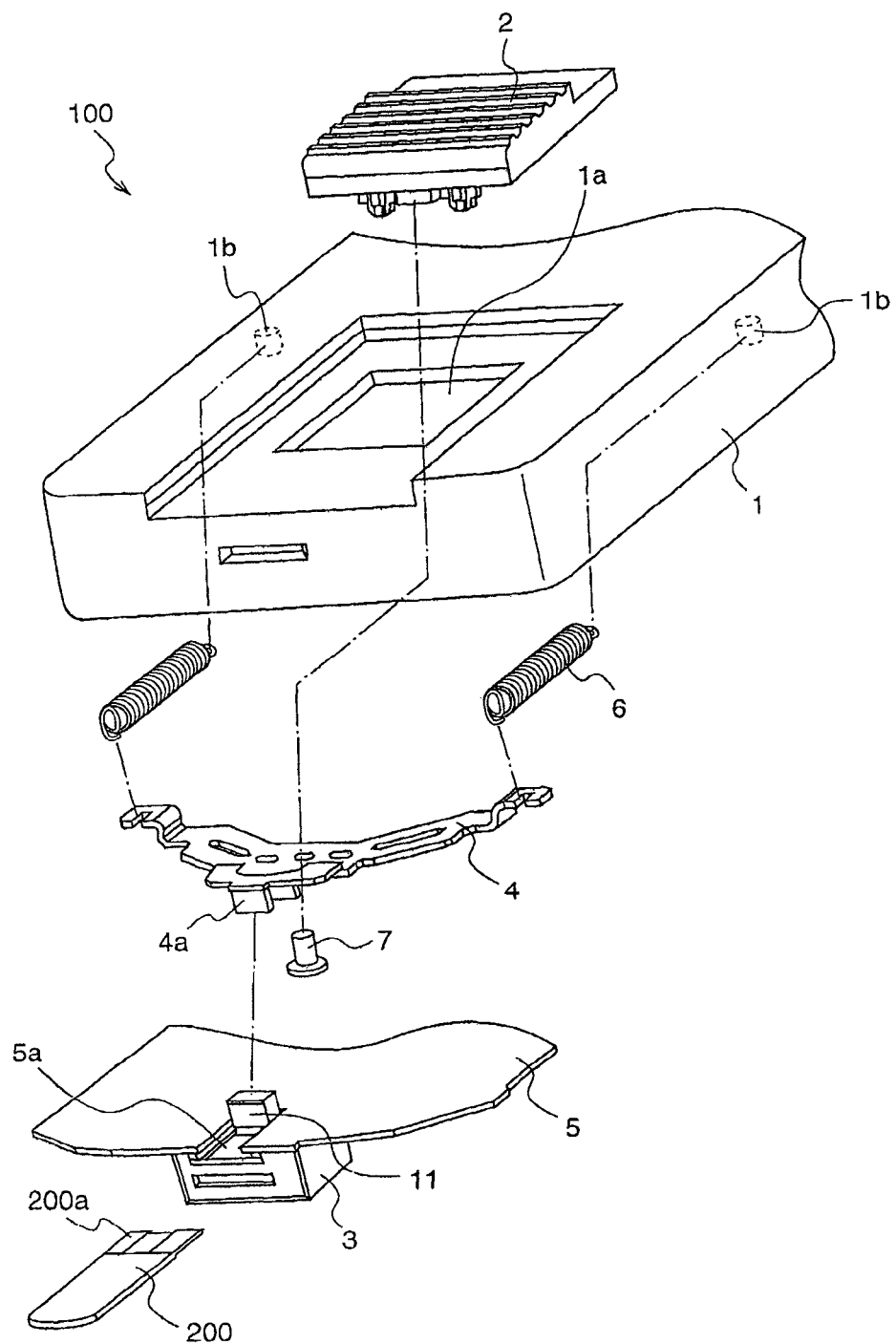
FIG. 1 is an exploded perspective view of a measurement device according to a first embodiment of the present invention.

DESCRIPTION OF REFERENCE NUMERALS 100,110,700 . . . measurement device
1 . . . main body
1a . . . rectangle hole
1b . . . boss
2 . . . ejection lever
2a . . . claw
2b . . . plastic spring
2c . . . slider fitting part
3,16,701 . . . connector
4 . . . interlocking member
4a . . . fitting part
5 . . . base plate
5a . . . notch
6 . . . spring
7 . . . screw
10 . . . sensor holding part
10a . . . notch
10b . . . hole 10c . . . connector port
11 . . . pushing member
11a . . . pushing member projection part
11b . . . projection part
12,20 . . . pushing member cover
13 . . . first brake part
14 . . . connection terminal
21 . . . second brake part
22 . . . support member
50 . . . solenoid
50a . . . iron core
51 . . . brake arm
51a . . . fulcrum point
51b . . . connection part
51c . . . third brake part
60 . . . eccentric cam
60a . . . shaft
60b . . . fourth brake part
60c . . . notch
61 . . . cam drive lever
61a . . . cam drive lever convex portion
70 . . . pump
71 . . . flow channel
71a . . . fifth brake part
200 . . . sensor
200a . . . electrode terminal
700a . . . display

DETAILED DESCRIPTION OF THE INVENTION

Hereinafter, preferred embodiments of measurement devices according to the present invention will be described in detail with reference to the drawings.

Embodiment 1

Hereinafter, a measurement device according to a first embodiment of the present invention will be described.

FIG. 1 is an exploded perspective view illustrating the measurement device of the first embodiment.

In FIG. 1, reference numeral 100 denotes a measurement device for measuring a sample such as body fluid which is applied to a sensor 200. Reference numeral 200 denotes a long and thin chip-shaped biosensor for collecting the sample to be analyzed.

The measurement device 100 includes a connector 3 which detachably supports the sensor 200 that is inserted from its front end, a connection terminal 14 which elastically contacts an electrode terminal 200a of the sensor 200 that is supported by the connector 3 to take out a signal required for analysis from the electrode terminal 200a of the sensor 200, an ejection mechanism which contacts the front side surface of the sensor 200 viewed from the measurement device and pushes the sensor 200 supported by the connector 3 forward while releasing the elastic contact between the electrode terminal 200a of the sensor 200 and the connection terminal 14, thereby to eject the sensor 200 from the connector 3, and a brake means which elastically contacts the sensor 200 to brake the movement of the sensor 200 in the ejection direction while the sensor 200 is pushed forward by the ejection mechanism.

The ejection mechanism comprises an ejection lever 2 and a pushing member 11.

The ejection lever 2 is inserted in a rectangle hole 1a of the measurement device body 1 so that it can be pushed out with respect to the measurement device body 1.

Further, an interlocking member 4 is hung on one ends of two springs 6 which are provided in parallel with each other at the both sides of the interlocking member 4 while the other ends of the springs 6 are hung on bosses 1b provided on both sides of the measurement device body 1. Further, a screw 7 is provided in the center of the bottom surface of the interlocking member 4, and thereby the interlocking member 4 is screwed to the center bottom portion of the ejection lever 2 via the chassis of the measurement device body 1.

A portion of the front end of the center part of the interlocking member 4 is U-shaped, and this U-shaped portion (fitting portion) 4a is fitted to the pushing member 11 which is housed in the connector 3. This pushing member 11 is a moving part of the ejection mechanism to be described later, and it can perform an operation of pushing the sensor 200 forward, i.e., the ejection direction of the sensor, in conjunction with the pushing lever 2. Therefore, when the ejection lever 2 is slid, the interlocking member 4 and the pushing member 11 are also slid in response to the sliding of the ejection lever 2.

The connector 3 is provided on a base plate 5. The base plate 5 and the measurement device body 1 are combined so that the pushing member 11 is slidably fitted in a notch 5a of the base plate 5, and the base plate 5 is screwed to the measurement device body 1.

Figure 2:
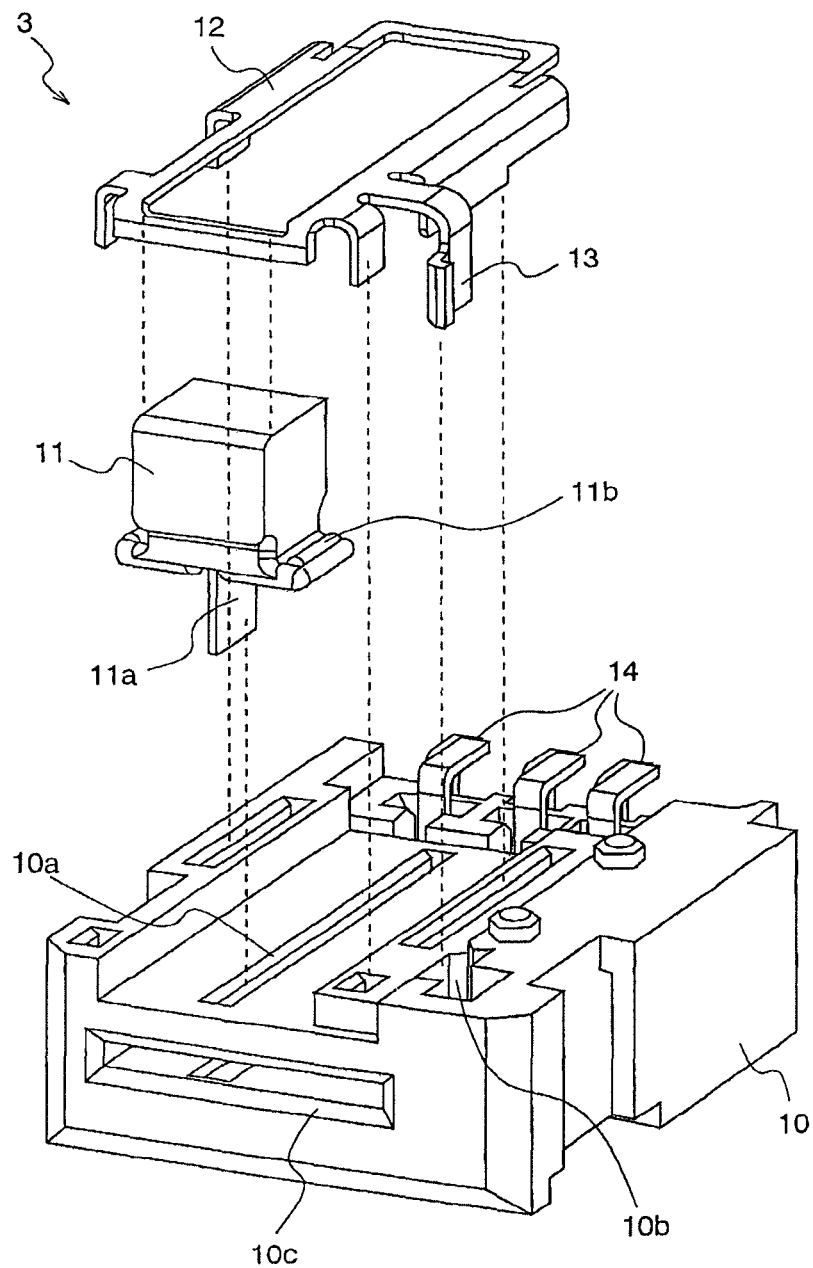
FIG. 2 is an exploded perspective view of a connector part of the measurement device of the first embodiment.

FIG. 2 is an exploded perspective view of the connector 3 of the measurement device 100 shown in FIG. 1.

With reference to FIG. 2, the connector 3 has a sensor holding part 10, a pushing member 11, and a pushing member cover 12.

The sensor holding part 10 has a connector port in which the sensor 200 is inserted, and a connection terminal 14 which elastically contacts the electrode terminal 200a of the sensor 200 to take out a signal required for analysis.

The pushing member 11 has a planar pushing member projection part 11a, and this pushing member projection part 11a is inserted in a notch 10a of the sensor holding part 10.

The pushing member cover 12 has a first brake part 13 comprising an elastic material. This first brake part 13 is provided at a position which contacts the side surface of the sensor 200, and housed in a hole 10b of the sensor holding part 10. Further, the first brake part 13 elastically contacts the side surface of the sensor 200 that is held by the sensor holding part 10, and thereby the movement speed of the sensor 200 in the ejection direction can be reduced by a frictional force that occurs between the first brake part 13 and the side surface of the sensor 200 when ejecting the sensor.

The pushing member cover 12 is fixed to the sensor holding part 10 so as to cover a projection part 11b of the pushing member 11. That is, the projection part 11b of the pushing member 11 is sandwiched between the pushing member cover 12 and the sensor holding part 10 with a predetermined space, and the pushing member 11 is, utilizing this sandwiched space, slidable within a range of the notch 10a of the sensor holding part 10. Accordingly, the pushing member 11 is slidable in the longitudinal direction of the notch 5a of the base plate 5 in response to the ejection lever 2.

While in this first embodiment the ejection mechanism for ejecting the sensor 200 and the brake means (first brake part 13) for braking the sensor 200 to be ejected are composed of different parts, the ejection mechanism may include the brake means.

Further, the first brake part 13 is placed contacting the sensor 200 at a sensor position where the contact of the connection terminal 14 with the electrode terminal 200a of the sensor 200 is released or at a sensor position which is by a predetermined amount anterior to the sensor position where the contact is released. In this case, since the first brake part 13 contacts the sensor 200 when the connection terminal 14 and the sensor electrode terminal 200a are completely separated from each other, the movement speed of the sensor in the ejection direction can be reliably reduced regardless of the pressing force of the connection terminal 14 to the sensor electrode terminal 200a.

In this first embodiment, the pushing member cover 12 is formed of a stainless material (SUS), and the first brake part 13 is formed in a shape that generates an elastic force by using the same SUS as the pushing member cover 12. This first brake part 13 has an elastic force with which it is bent within a range of 0.05 mm to 0.25 mm by the contact with the side surface of the sensor 22, and the contact pressure applied to the side surface of the sensor 200 at this time is 40 g to 60 g.

The thickness of the sensor 200 is 0.18 mm to 0.44 mm, the width of the sensor 200 is 6.6 mm, and the width of the connector port 10c is 6.8 mm. While the first brake part 13 is formed of the stainless material (SUS) that is the same metal material as the pushing member cover 12, it may be formed of a plastic material. For example, an elastic plastic material is used as a material of the first brake part 13, and a resistance is given to the sensor 200 by using the elastic force of the plastic material to brake the movement of the sensor 200 in the ejection direction. As the plastic material, for example, POM (polyacetal) or ABS (acrylonitrile butadiene styrene) can be used. Alternatively, an elastic force of a rubber material may be used. For example, nitrile rubber (NBR), chloroprene buffer (CR), urethane rubber (U), silicon rubber (Q), or fluorine-containing rubber (FKM) may be used.

Next, the sensor ejection method for ejecting the sensor 200 from the measurement device 100 will be described with reference to FIGS. 1, 2, 3, 6, and 10.

When the sensor 200 is inserted in the connector 3, the electrode terminal 200a of the sensor 200 elastically receives a contact pressure from above by the connection terminal 14 provided in the connector 3, and thereby the sensor 200 is held in the connector 3. After the sensor 200 is inserted in the measurement device 100, a sample such as body fluid is applied to the front end of the sensor 200 to perform measurement. Thereafter, the sensor 200 is ejected from the measurement device 100 as follows.

Figure 3:
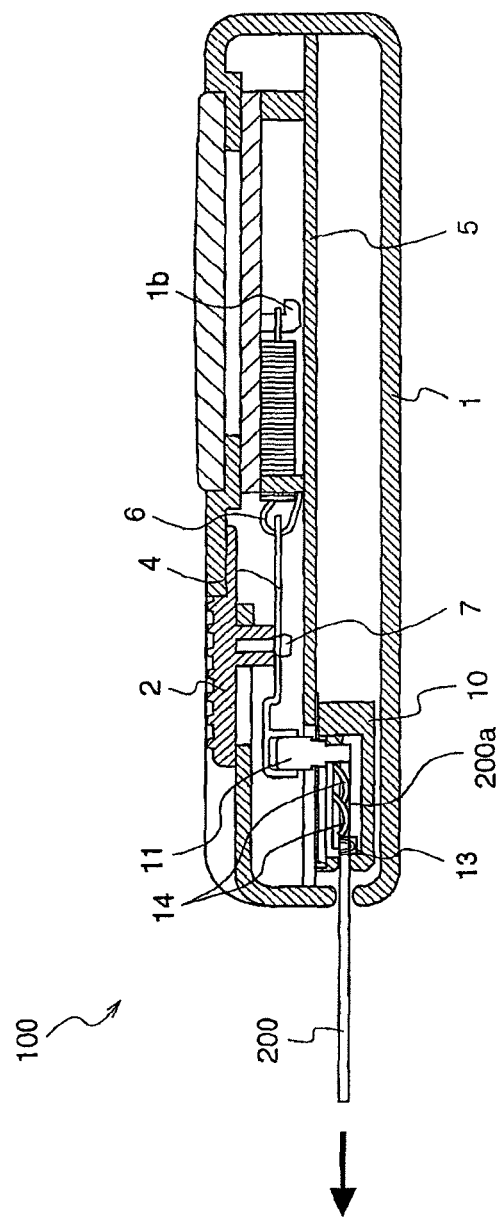
FIG. 3 is a cross-sectional view of the measurement device of the first embodiment.

Initially, the operator slides the ejection lever 2 with his finger in the direction of arrow shown in FIG. 3, i.e., the ejection direction (step S101). Then, the interlocking member 4 which is attached to the ejection lever 2 with the screw 7 moves in conjunction with the ejection lever 2. At this time, since the U-shaped front end of the interlocking member 4 is fitted to the pushing member 11 of the connector 3, the pushing member 11 can be slid by sliding the ejection lever 2.

When the pushing member 11 is slid in the arrow direction in response to the ejection lever 2, the end surface of the sensor 200 is pushed and thereby the connection between the electrode terminal 200a of the sensor 200 and the connection terminal 14 in the sensor holding part 10 is released (step S102). At this time, the sensor 200 is flipped by the connection terminal 14 in the ejection direction. This is caused by that the sensor 200 is generally thin and flat in shape, and that the connection terminal 14 has a restoring force which tries to return the connection terminal 14 to the shape before the contact at the moment when the connection between the sensor electrode terminal 200 and the connection terminal 14 is released, and the sensor 200 is flipped by this restoring force in the ejection direction. Further, since the ejection lever 2 is slid to eject the sensor by the pushing member 11 which moves in response to the ejection lever 2 with the electrode terminal 200a of the sensor 200 being elastically pressed from above by the connection terminal 14, a force which directly pushes the sensor 200 with the pushing member 11 is generated in addition to the force which flips the sensor 200 in the ejection direction with the connection terminal 14 as the speed of sliding the ejection lever 2 is increased.

In this first embodiment, since the first brake part 13 of the pushing member cover 12 provided in the connector 3 contacts the side surface of the sensor 200 that is held by the sensor holding part 10, the movement of the sensor 200 in the ejection direction is braked by the frictional force that occurs between the first brake part 13 and the side surface of the sensor 200 when ejecting the sensor (step S103). At this time, the ejection speed of the sensor 200 at the timing when the sensor 200 is separated from the connector 3 is a speed V2 shown in FIG. 6 which is by far lower than the conventional speed with which the sensor 200 is excessively jumped out, and therefore, it is possible to prevent the sensor 200 from being ejected with a speed which is not intended by the operator.

Then, the sensor 200 is ejected from the measurement device body 1 (step S104), and the operator releases the ejection lever 2, i.e., cancels the force applied to the ejection lever 2 (step S105), whereby the interlocking member 4 is automatically returned to the initial setting position before the ejection operation of the sensor 200 by the restoring force of the spring 6.

Since the above-described sequence of operations can prevent the sensor 200 from jumping out with a speed which is not expected by the operator, the sensor 200 can be safely ejected to be discarded.

As described above, the measurement device 100 of this first embodiment includes the ejection mechanism comprising the ejection lever 2 which is slidably attached to the measurement device body 1, and the pushing member 11 which pushes the sensor 200 in response to the ejection lever 2, and the first brake part 13 comprising an elastic material is brought into contact with the side surface of the sensor 200. Therefore, when ejecting the sensor by the ejection mechanism, the movement of the sensor in the ejection direction can be braked, and thereby the sensor is prevented from rapidly jumping out in an unintended direction when it is ejected. Further, the operator can discard the sensor without touching the sample attached to the sensor, and the sensor 200 is prevented from jumping out with an excessive speed which cannot be expected by the operator. As the result, infection of disease or the like can be avoided, and the reliability of the sensor at disposal can be enhanced.

Further, according to the measurement device 100 of this first embodiment, since the first brake part 13 is provided at the position which contacts the side surface of the sensor 200, the configuration of the brake means can be simplified without the necessity of adopting the complicated configuration that the brake means is brought into contact with the sensor only when ejecting the sensor. Further, since, when ejecting the sensor 200, the first brake part 13 contacts the sensor 200 before and after the connection between the sensor electrode terminal 200a and the connection terminal 14 is released, the movement of the sensor 200 in the ejection direction can be reliably braked regardless of the pressing force of the connection terminal 14 to the sensor electrode terminal 200a.

Further, even when the speed of sliding the ejection lever 2 is increased and thereby a force which tries to push the sensor 200 in the ejection direction is applied, the movement of the sensor 200 in the ejection direction can be reliably braked by the first brake part 13.

Furthermore, according to the measurement device 100 of the first embodiment, since the first brake part 13 is placed inside the sensor holding part 10, the number of parts of the connector 3 can be reduced and thereby the size of the connector 3 can be reduced.

While in this first embodiment the first brake part 13 is provided at only one side of the pushing member cover 12 so as to contact the one side surface of the sensor 200, it may be provided at the both sides of the pushing member cover 12 so as to contact the both side surfaces of the sensor 200. In this case, since the sensor 200 is braked at its both side surfaces, the orientation of the sensor 200 to be ejected becomes less polarized, and thereby the sensor 200 can be ejected more linearly.

Further, while in this first embodiment the first brake part 13 contacts the side surface of the sensor, it may contact one plane surface of the sensor with the same effects as described above.

Embodiment 2

Hereinafter, a second embodiment of the present invention will be described with reference to the drawings.

Figure 5:
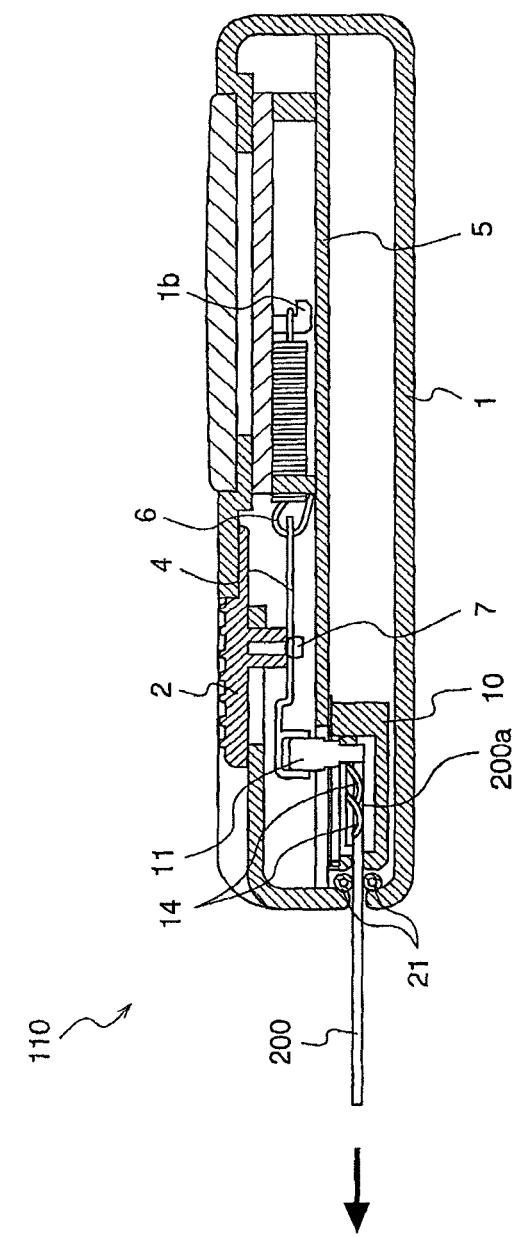
FIG. 5 is a cross-sectional view of the measurement device of the second embodiment.
Figure 6:
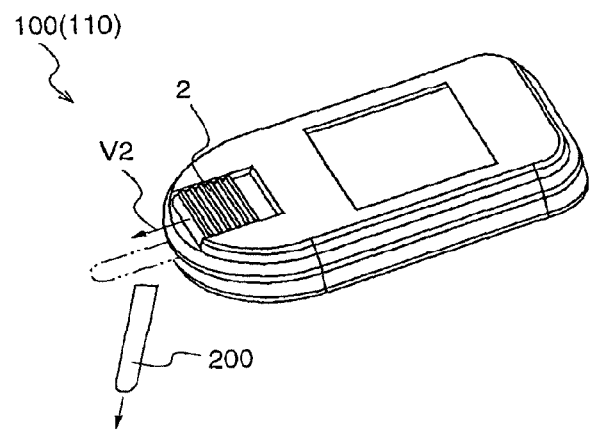
FIG. 6 is a schematic diagram of the measurement device of the first or second embodiment during sensor ejection.

FIG. 5 is a cross-sectional view of a measurement device 110 of this second embodiment.

In FIG. 5, reference numeral 110 denotes a measurement device for measuring a sample such as body fluid that is applied to a sensor 200. Reference numeral 200 denotes a long and thin chip-shaped biosensor for collecting the sample to be analyzed.

The fundamental configuration of the measurement device 110 of this second embodiment is identical to that of the measurement device 100 of the first embodiment shown in FIG. 1.

That is, the measurement device 110 includes a connector 3 which detachably supports the sensor 200 that is inserted from its front end, a connection terminal 14 which elastically contacts an electrode terminal 200a of the sensor 200 that is supported by the connector 3 to take out a signal required for analysis from the electrode terminal 200a of the sensor 200, an ejection mechanism which contacts the front side surface of the sensor 200 viewed from the measurement device side and pushes the sensor 200 supported by the connector 3 forward while releasing the elastic connection between the electrode terminal 200a of the sensor 200 and the connection terminal 14, thereby to eject the sensor 200 from the connector 3, and a brake means which elastically contacts the sensor 200 to brake the movement of the sensor 200 in the ejection direction when the sensor 200 is pushed forward by the ejection mechanism.

The ejection mechanism comprises an ejection lever 2 and a pushing member 11.

The ejection lever 2 is inserted in a rectangle hole 1a of the measurement device body 1 so as to be slidably attached to the measurement device body 1.

Further, an interlocking member 4 is hung on one ends of two springs 6 which are provided in parallel with each other at the both sides of the interlocking member 4 while the other ends of the springs 6 are hung on bosses 1b provided on the both sides of the measurement device body 1. Further, a screw 7 is provided in the center of the bottom surface of the interlocking member 4, and thereby the interlocking member 4 is screwed to the center bottom surface of the ejection lever 2 via the chassis of the measurement device body 1.

A portion of the front end of the center part of the interlocking member 4 is U-shaped, and this U-shaped portion (fitting portion) 4a is fitted to the pushing member 11 which is housed in the connector 3. This pushing member 11 is a moving part of the ejection mechanism to be described later, and it can perform the sensor pushing operation in the forward direction, i.e., in the sensor ejection direction, in conjunction with the pushing lever 2. Therefore, when the ejection lever 2 is slid, the interlocking member 4 and the pushing member 11 are also slid in response to the sliding of the ejection lever 2.

The connector 3 is provided on a base plate 5. The base plate 5 and the measurement device body 1 are combined such that the pushing member 11 is slidable in a notch 5a of the base plate 5, and the base plate 5 is screwed to the measurement device body 1.

Figure 4:
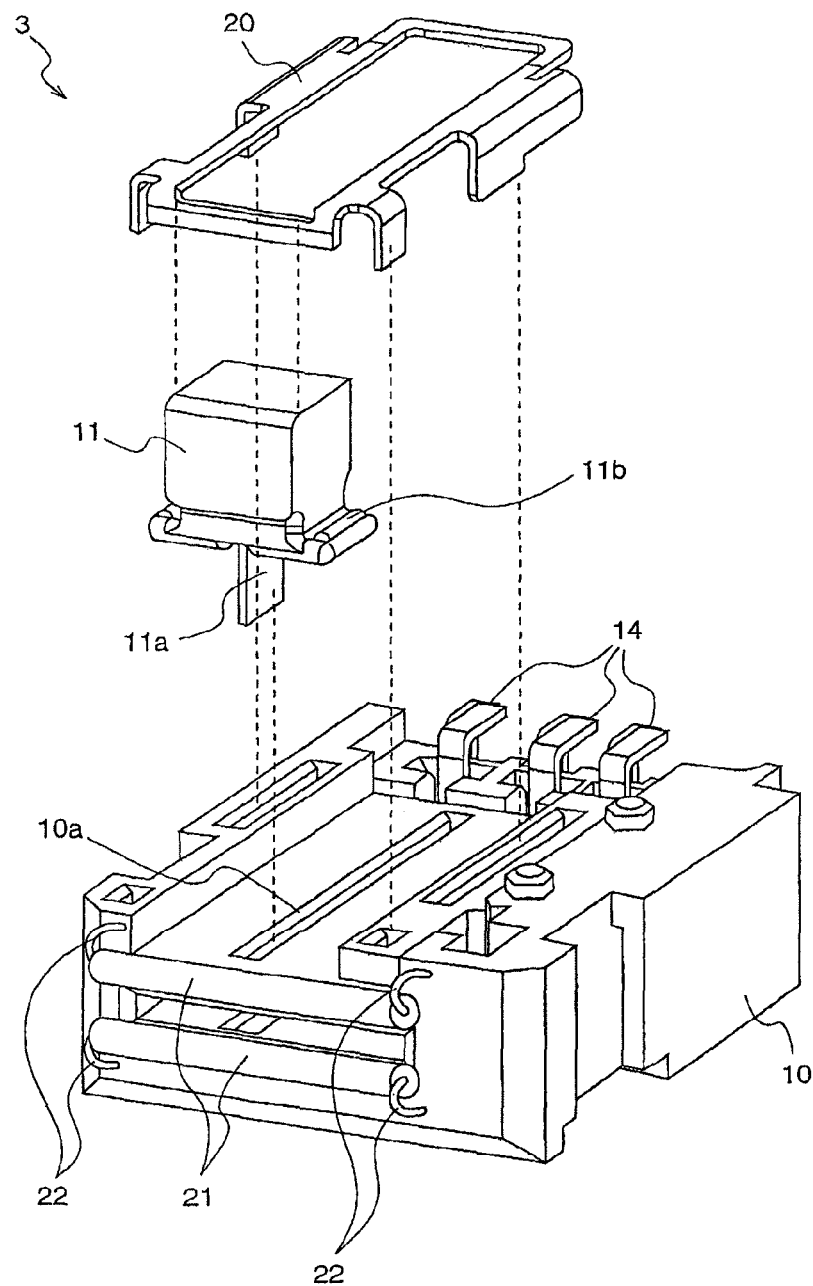
FIG. 4 is an exploded perspective view of a connector part of a measurement device according to a second embodiment of the present invention.

FIG. 4 is an exploded perspective view of the connector 3 in the measurement device 110 of this second embodiment.

With reference to FIG. 4, the connector 3 has a sensor holding part 10, a pushing member 11, and a pushing member cover 20.

The pushing member 11 has a planar pushing member projection part 11a, and this pushing member projection part 11a is inserted in a notch 10a of the sensor holding part 10.

The pushing member cover 12 is fixed to the sensor holding part 10 so as to cover a projection part 11b of the pushing member 11. That is, the projection part 11b of the pushing member 11 is sandwiched between the pushing member cover 20 and the sensor holding part 10 with a predetermined space, and the pushing member 11 is, using this space, slidable within the range of the notch 10a of the sensor holding part 10. Accordingly, the pushing member 11 is slidable in the longitudinal direction of the notch 5a of the base plate 5 in response to the ejection lever 2.

By the way, the measurement device 110 of this second embodiment is different from the measurement device 100 of the first embodiment in the configuration and position of the brake means which brakes the movement of the sensor in the ejection direction. That is, while the first brake part 13 is provided on the pushing member cover 12 in the measurement device 100 of the first embodiment, the measurement device 110 of this second embodiment has second brake parts 21 disposed outside the connector port 10c which is the sensor insertion port of the sensor holding part 10.

The second brake parts 21 are rotating bodies provided at a position contacting a plane surface of the sensor 200, which are rotatably supported by a support member 22 at the upper and lower sides of the connector port 10c.

The second brake parts 21 elastically contact the upper and lower surfaces of the sensor 200 which is held by the sensor holding part 10, the two second brake parts 21 are rotated when ejecting the sensor, and the movement speed of the sensor 200 in the ejection direction is decreased by a frictional force that is generated between each of the second brake parts 21 and the plane surface of the sensor 200. As for the specific configuration of the second brake parts 21 in this second embodiment, each second brake part 21 has a diameter of 3 mm and a length of 10 mm, and POM (polyacetal) or ABS (acrylonitrile butadiene styrene) is used as the material thereof. The second brake parts 21 apply a load of 40 g to 60 g to the sensor 200 when the sensor 200 passes through them.

While in this second embodiment the second brake parts 21 are provided at the two positions above and beneath the sensor insertion port of the sensor holding part 10, one second brake part 21 may be provided either above or beneath the sensor insertion port, or the second brake parts 21 may be configured so as to contact the side surfaces of the sensor 200.

While in this second embodiment the second brake parts 21 are provided outside the sensor insertion port of the sensor holding part 10, the brake parts 21 may be provided inside the sensor insertion port on the measurement device body 1 side.

Further, the second brake parts 21 are brought into contact with the sensor 200 at the sensor position where the contact of the connection terminal 14 with the electrode terminal 200*a* of the sensor 200 is released or at the sensor position which is by a predetermined amount anterior to the sensor position where the contact is released. Thereby, since the second brake parts 21 contact the sensor 200 after the connection terminal 14 and the sensor electrode terminal 200*a* are completely separated from each other, the movement speed of the sensor in the ejection direction can be reliably decreased regardless of the pressing force of the connection terminal 14 to the sensor electrode terminal 200*a*.

Figure 11:
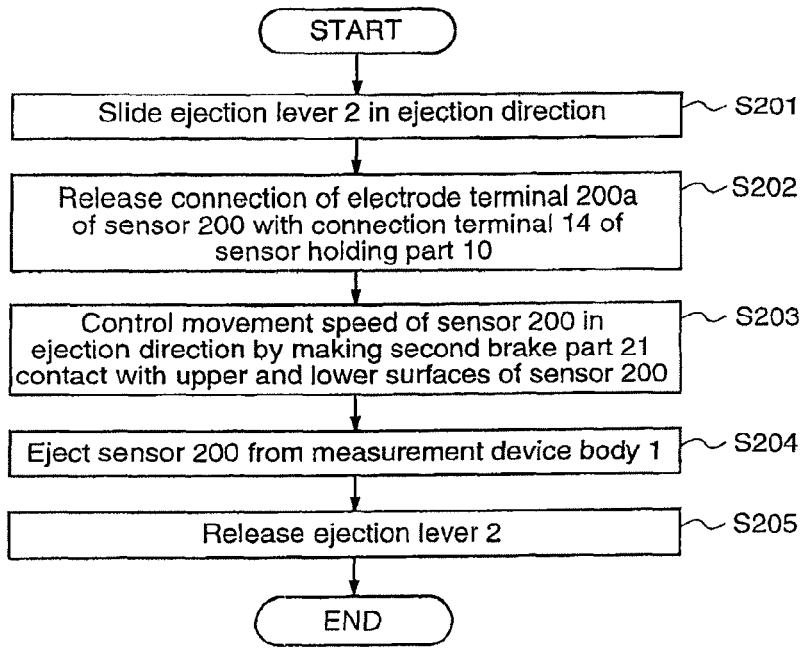
FIG. 11 is a flowchart for explaining a sensor ejection method of the second embodiment.

Next, the sensor ejection method for ejecting the sensor 200 from the measurement device 110 will be described with reference to FIGS. 4, 5, and 11.

When the sensor 200 is inserted in the connector 3, the electrode terminal 200*a* of the sensor 200 elastically receives a contact pressure from above by the connection terminal 14 provided in the connector 3, and thereby the sensor 200 is held in the connector 3. After the sensor 200 is thus inserted in the measurement device 110, a sample such as body fluid is applied to the front end of the sensor 200 to perform measurement. Thereafter, the sensor 200 is ejected from the measurement device 110 as follows.

Initially, the operator slides the ejection lever 2 with his finger in the direction of arrow shown in FIG. 5, i.e., the ejection direction (step S201). Then, the interlocking member 4 which is attached to the ejection lever 2 with the screw 7 moves in conjunction with the ejection lever 2. At this time, since the U-shaped front end of the interlocking member 4 is fitted to the pushing member 11 of the connector 3, the pushing member 11 can be slid by sliding the ejection lever 2.

When the pushing member 11 is slid in the arrow direction in response to the ejection lever 2, the end surface of the sensor 200 is pushed and thereby the connection between the electrode terminal 200*a* of the sensor 200 and the connection terminal 14 in the sensor holding part 10 is released (step S202). At this time, the sensor 200 is flipped in the ejection direction by the connection terminal 14. This is caused by that the sensor 200 is generally thin and flat in shape, and that the connection terminal 14 has a restoring force which tries to return the connection terminal 14 to the shape before the contact at the moment when the connection between the sensor electrode terminal 200 and the connection terminal 14 is released, and the sensor 200 is flipped in the ejection direction by this restoring force. Further, since the ejection lever 2 is slid to eject the sensor by the pushing member 11 which moves in response to the ejection lever 2 with the electrode terminal 200*a* of the sensor 200 being elastically pressed from above by the connection terminal 14, a force which directly pushes the sensor 200 with the pushing member 11 is generated in addition to the force which flips the sensor 200 in the ejection direction with the connection terminal 14 as the speed of sliding the ejection lever 2 is increased.

In this second embodiment, since the second brake parts 21 provided on the sensor holding part 10 contact the upper and lower surfaces of the sensor 200, the movement of the sensor 200 in the ejection direction is braked by the frictions between the second brake parts 21 and the upper and lower surfaces of the sensor 200 (step S203). Thereby, the ejection speed of the sensor 200 at the timing when the sensor 200 is separated from the connector 3 is a speed V2 shown in FIG. 6 which is by far lower than the speed with which the sensor 200 is excessively jumped out, and thereby the sensor 200 is prevented from being ejected with a speed that is not intended by the operator.

Then, the sensor 200 is ejected from the measurement device body 1 (step S204), and the operator releases the ejection lever 2, i.e., cancels the force applied to the ejection lever 2 (step S205), whereby the interlocking member 4 is automatically returned to the initial setting position before the ejection operation of the sensor 200 by the restoring force of the springs 6.

Since the above-described sequence of operations can prevent the sensor 200 from jumping out with a speed that cannot be expected by the operator, the sensor 200 can be safely ejected to be discarded.

As described above, the measurement device 110 of this second embodiment includes the ejection mechanism comprising the ejection lever 2 which is slidably attached to the measurement device body 1, and the pushing member 11 which pushes the sensor 200 in response to the ejection lever 2, and the second brake parts 21 as the rotating bodies comprising a plastic material are rotatably supported in the vicinity of the sensor ejection port so as to be brought into contact with the flat surfaces of the sensor. Therefore, the movement of the sensor in the ejection direction can be braked by applying a load onto the flat surfaces of the sensor to be ejected, and thereby the sensor is prevented from being rapidly ejected in an unintended direction. As the result, the operator can discard the sensor without touching the sample attached to the sensor, and the sensor can be prevented from being ejected with an excessive speed which cannot be expected by the operation.

Further, according to the measurement device 100 of this second embodiment, since the second brake parts 21 are provided outside the connector port 10*a* so as to be brought in contact with the flat surfaces of the sensor 200, the configuration of the brake means can be simplified without the necessity of adopting the complicated configuration that the brake means is brought into contact with the sensor only when ejecting the sensor. Further, since, when ejecting the sensor 20, the second brake parts 21 contact the sensor 200 before and after the connection between the electrode terminal 200*a* of the sensor 200 and the connection terminal 14 is released, the movement of the sensor in the ejection direction can be reliably braked regardless of the pressing force of the connection terminal 14 to the sensor electrode terminal 200*a*.

Furthermore, in the measurement device 110 of this second embodiment, since the second brake parts 21 are provided outside the connector, the contact region to the sensor can be increased relative to the first brake part 13 of the first embodiment, and thereby the measurement device 110 can be configured with relatively rough dimensions of components.

Moreover, according to the measurement device 110 of this second embodiment, even when the speed of sliding the ejection lever 2 is increased and thereby a force which tries to push the sensor 200 in the ejection direction is applied, the movement of the sensor 200 in the ejection direction can be reliably braked by the second brake parts 21.

The configuration of the brake means of the present invention is not limited to the planar one and the rotating bodies which are described in the first and second embodiments, respectively, it may have any shape and it may be located at any position so long as it is configured according to the purpose of braking the movement of the sensor in the ejection direction.

Embodiment 3

Hereinafter, a measurement device according to a third embodiment of the present invention will be described.

The measurement device of this third embodiment utilizes an operation means comprising a solenoid 50 as the brake mechanism for braking the movement of the sensor in the ejection direction.

Figure 7:
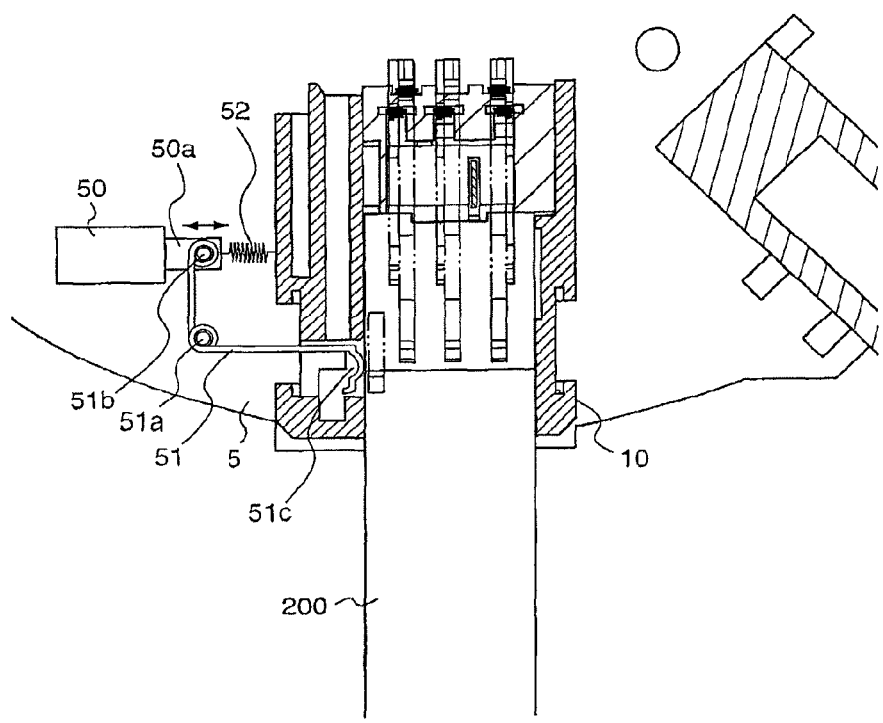
FIG. 7 is an exploded plan view of a connector part of a measurement device according to a third embodiment of the present invention.

FIG. 7 is a plan view of the measurement device of this third embodiment.

In FIG. 7, a solenoid 50 is connected to the connector 3 provided on the base plate 5, and an it is electrically turned ON and OFF according to the position of the ejection lever 2 to slide its iron core 50a right to left. In this third embodiment, the direction in which the iron core 50a approaches the sensor holding part of the connector 3 is the right direction, while the direction in which the iron core 50a goes away from the sensor holding part is the left direction.

A brake arm 51 is rotatable around a fulcrum point 51a, and has a connection part 51b at its one end and a third brake part 51c at the other end. The connection part 51b is connected to a portion of the iron core 50, and the third brake part 51c can be brought into contact with a portion of the sensor 20 by the operation of the solenoid 50.

A return spring 52 pulls the iron core 50a in the right direction, and the iron core 50a is at the rightward slid position and the third brake part 51c does not contact the sensor 200 when the solenoid 50 is electrically OFF.

Since the fundamental structure of the measurement device is identical to those described for the first and second embodiments excluding the brake means, repeated description is not necessary.

Figure 12:
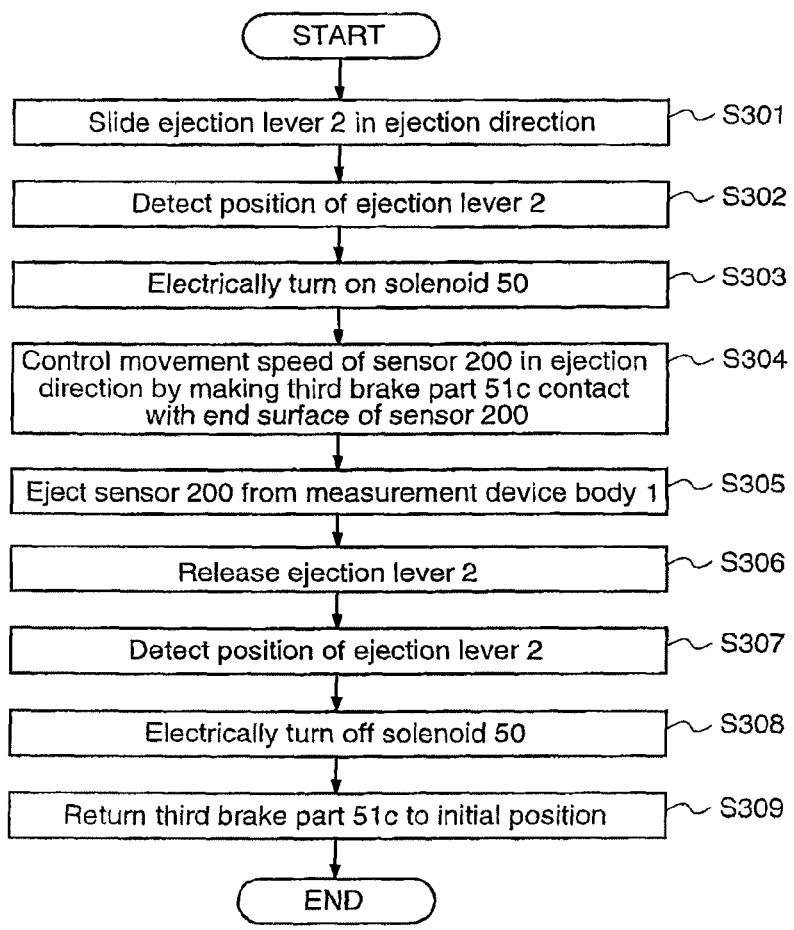
FIG. 12 is a flowchart for explaining a sensor ejection method of the third embodiment.

Next, a sensor ejection method for ejecting the sensor 200 from the measurement device will be described with reference to FIGS. 3, 7, and 12.

Initially, the operator slides the ejection lever 2 with his finger in the direction of arrow shown in FIG. 3, i.e., in the ejection direction (step S301). A position detection switch (not shown) for detecting the position of the ejection lever 2 is changed from ON to OFF or from OFF to ON according to the position of the ejection lever 2 (step S302). When the solenoid 50 is electrically turned ON according to the output of the position detection switch (step S303), the iron core 50a moves in the left direction overcoming the load of the return spring 52. According to this operation, a brake arm 51 that is movable in conjunction with the solenoid is rotated counterclockwise around the fulcrum point 51a, and thereby the third brake part 51c contacts the end surface of the sensor 200 to function as a brake force (step S304).

After the sensor 200 is ejected from the measurement device body 1 (step S305), when the operator releases the ejection lever 2, i.e., cancels the force applied to the ejection lever 2 (step S306), the ejection lever 2 is returned to the original position. When it is detected that the position detection switch is turned ON or OFF (step S307), the solenoid 50 is electrically turned OFF (step S308). Then, the iron core 50a is pulled in the right direction by the return spring 52 and returned to the original position. At this time, the brake arm 51 is rotated clockwise around the fulcrum point 51a, and the third brake part 51a is returned to the original position (step S309). Accordingly, when a new sensor 200 is inserted, the third brake part 51c does not contact the end surface of the sensor 200.

Since the material of the third brake part 51c is identical to that of the first brake part 13 of the first embodiment, repeated description is not necessary.

As described above, the measurement device of this third embodiment includes the switch for detecting the position of the ejection lever 2 that is slidably attached to the measurement device body 1, and the solenoid 50 is operated according to the output of the position detection switch to bring the third brake part 51c comprising an elastic material into contact with the side surface of the sensor 200 so as to brake the movement of the sensor 200 in the ejection direction, and thus the sensor is prevented from rapidly jumping out of in an unintended direction when ejecting the sensor. Therefore, it is possible to prevent the sensor 200 from jumping out with an excessive speed the operator cannot expect, and the operator can safely discard the sensor without touching the sample attached to the sensor by mistake, and thereby, even when the sample contains a disease agent, secondary infection of disease or the like can be avoided to enhance the reliability when discarding the sensor.

Further, according to the measurement device of this third embodiment, only when ejecting the sensor, the ejection mechanism is operated to bring the third brake part 51c into contact with a portion of the sensor 200 so as to exert the brake force of the third brake part 51a on the sensor 200. Therefore, the third brake part 51c does not perform unnecessary operation except when ejecting the sensor, and it can brake the movement of the sensor in the ejection direction with the minimum operation. Further, since the brake part does not contact the end surface of the sensor when a new sensor is inserted, the sensor can be smoothly inserted in the measurement device without applying an excessive load to the sensor.

Embodiment 4

Hereinafter, a measurement device according to a fourth embodiment of the present invention will be described.

The measurement device of this fourth embodiment utilizes an eccentric cam as a brake mechanism for braking the movement of the sensor in the ejection direction.

Figure 8:
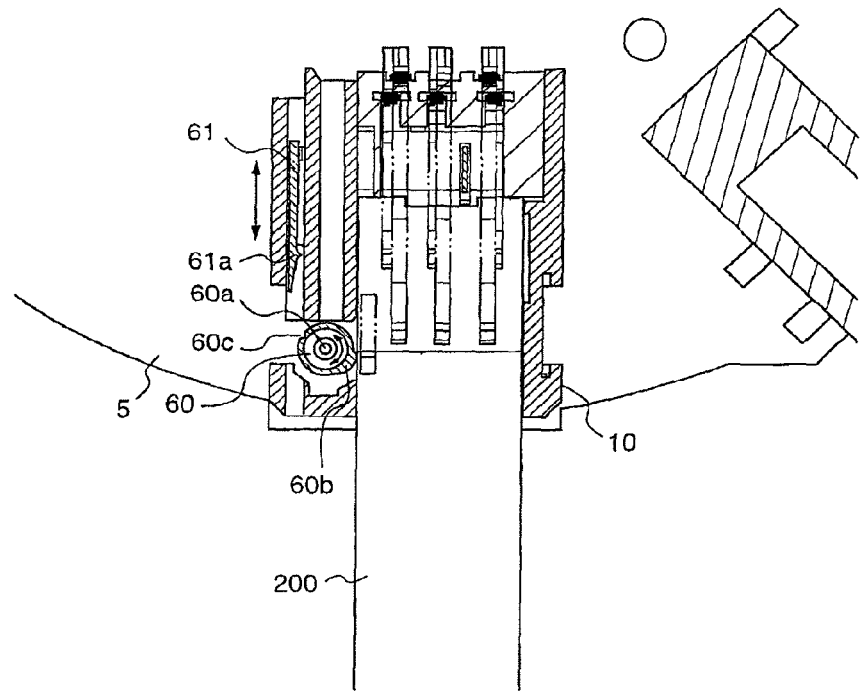
FIG. 8 is an exploded plan view of a connector part of a measurement device according to a fourth embodiment of the present invention.

FIG. 8 is a plan view of the measurement device of the fourth embodiment.

In FIG. 8, an eccentric cam 60 is rotatable around a shaft 60a, and has a fourth brake part 60b that is partially protruded and a notch 60c that is partially concave.

A cam drive lever 61 has a cam drive lever convex part 61a that can be engaged with the notch 60c. The cam drive lever 61 is coordinated with the ejection lever 2 which is not shown.

Since the fundamental structure of the measurement device is identical to those described for the first and second embodiments excluding the brake means, repeated description is not necessary.

Figure 13:
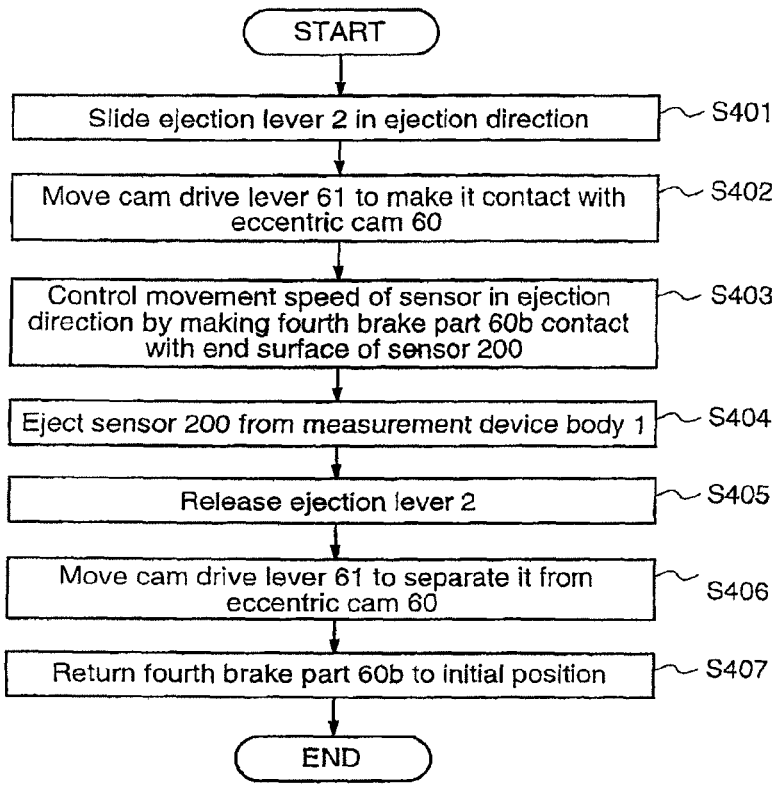
FIG. 13 is a flowchart for explaining a sensor ejection method of the fourth embodiment.

Next, a sensor ejection method for ejecting the sensor 200 from the measurement device will be described with reference to FIGS. 3, 8, and 13.

Initially, the operator slides the ejection lever 2 with his finger in the direction of arrow shown in FIG. 3, i.e., in the ejection direction (step S401). Then, the cam drive lever 61 is slid in conjunction with the ejection lever 2 downward in FIG. 8, i.e., in the direction which approaches the eccentric cam 60, and thereby the cam drive lever 61 contacts the eccentric cam 60 (step S402). Then, the cam drive lever convex part 61a is engaged with the notch 60c, the eccentric cam 60 is rotated counterclockwise around the shaft 60a, and the fourth brake part 60b comprising an elastic material elastically contacts the end surface of the sensor 200 to function as a brake force (step S403).

After the sensor 200 is ejected from the measurement device body 1 (step S404), when the operator releases the ejection lever 2, that is, chancels the force applied to the ejection lever 2 (step S405), the ejection lever 2 is returned to the original position. In conjunction with the ejection lever 2, the cam drive lever 61 is slid upward in FIG. 8, i.e., in the direction which goes away from the eccentric cam 60, and the eccentric cam 60 is rotated clockwise around the shaft 60a and thereby the cam drive lever convex part 61a is separated from the notch 60c (step S406). The cam drive lever 61 returns to the original position, and the fourth brake part 60b also returns to the initial position (step S406). Accordingly, when a new sensor 200 is inserted, the fourth brake part 60b does not contact the end surface of the sensor 200, and thus the sensor can be smoothly inserted in the measurement device without applying an excessive load to the sensor.

The material of the eccentric cam convex part 60b at which the eccentric cam 60 contacts the sensor 200 is not restricted to the stainless material (SUS) which is the same metal material as that for the pushing member cover 12, but it may be a plastic material. For example, using an elastic plastic material, a resistance may be applied to the sensor 200 utilizing the elastic force of the plastic material to brake the movement of the sensor 200 in the ejection direction. As the plastic material, for example, POM (polyacetal) or ABS (acrylonitrile butadiene styrene) can be used. Alternatively, an elastic force of a rubber material may be used. For example, nitrile rubber (NBR), chloroprene buffer (CR), urethane rubber (U), silicon rubber (Q), or fluorine-containing rubber (FKM) may be used.

As described above, according to the measurement device of this fourth embodiment, the ejection lever 2 is slid to bring the cam drive lever 61 into contact with the eccentric cam 60, and the eccentric cam 60 is rotated around the shaft 60a to bring the fourth brake part 60b which is the convex portion of the eccentric cam 60 in elastic contact with a portion of the sensor 200, thereby to brake the movement of the sensor 200 in the ejection direction. Therefore, the sensor is prevented from rapidly jumping out in an unintended direction when ejecting the sensor. Accordingly, it is possible to prevent the sensor 200 from jumping out with an excessive speed the operator cannot expect. As the result, when the sample contains a disease agent, the operator can safely discard the sensor without touching the sample attached to the sensor, and thereby secondary infection of disease or the like can be avoided to enhance the reliability when discarding the sensor.

Further, according to the measurement device of this fourth embodiment, only when ejecting the sensor, the ejection mechanism is operated to bring the fourth brake part 60b into contact with a portion of the sensor 200 so as to exert the brake force of the fourth brake part 60b on the sensor 200. Therefore, the fourth brake part 60b does not perform unnecessary operation except when ejecting the sensor, and it can brake the movement of the sensor in the ejection direction with the minimum operation. Further, since the brake part does not contact the end surface of the sensor when a new sensor is inserted, the sensor can be smoothly inserted in the measurement device without applying an excessive load to the sensor. Moreover, since the ejection mechanism and the brake means are operated in conjunction with each other, the battery energy is not wasted.

Embodiment 5

Hereinafter, a fifth embodiment of the present invention will be described with reference to the drawings.

A measurement device of this fourth embodiment adopts a pump as a brake mechanism for braking the movement of the sensor in the ejection direction.

Figure 9:
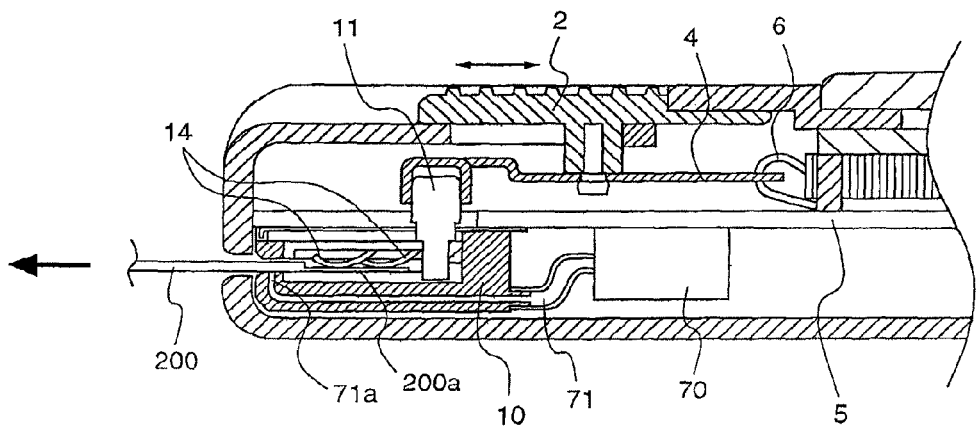
FIG. 9 is a cross-sectional view of a measurement device according to a fifth embodiment of the present invention.
Figure 10:
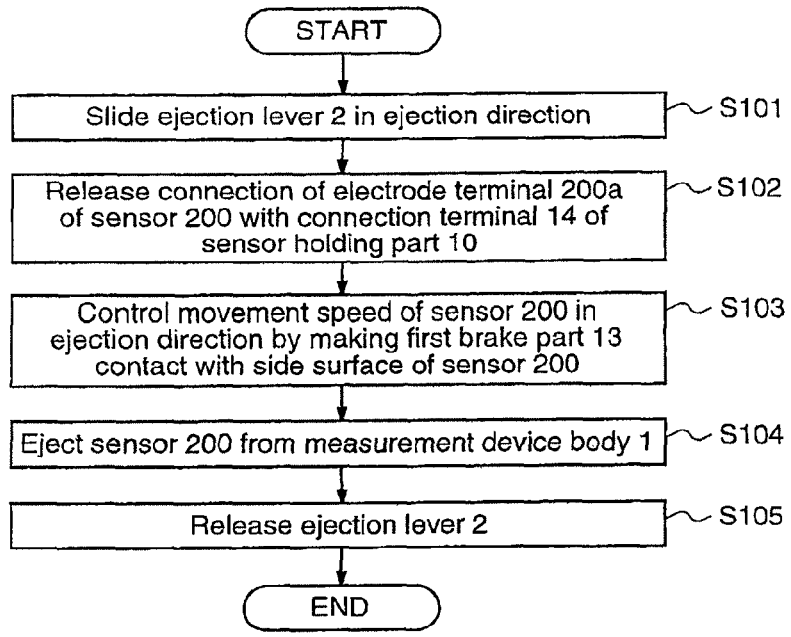
FIG. 10 is a flowchart for explaining a sensor ejection method of the first embodiment.

FIG. 9 is a cross-sectional view of the measurement device of this fifth embodiment.

In FIG. 9, a pump 70 is connected to the circuit on the base plate 5, and it is electrically turned ON and OFF to perform suction or exhaust of air, or stop the suction or exhaust.

A flow channel 71 is connected to the pump 70 at its one end, and the other end as a brake part 71a is connected to a vent hole which is provided in the measurement device body 1 opposed to the flat surface of the sensor 200.

Since the fundamental structure of this measurement device is identical to those described for the first and second embodiments excluding the brake means, repeated description is not necessary.

Figure 14:
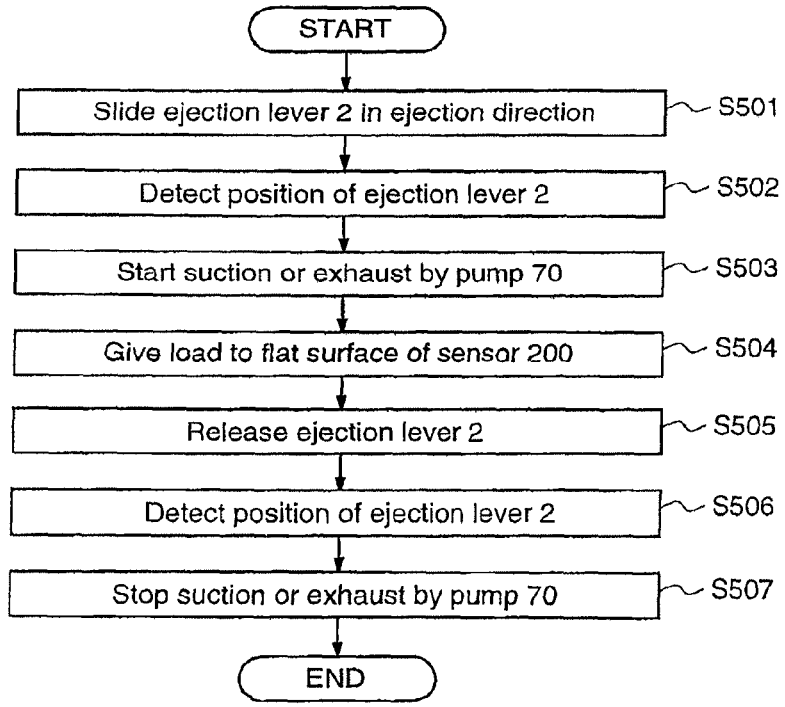
FIG. 14 is a flowchart for explaining a sensor ejection method of the fifth embodiment.
Figure 15:
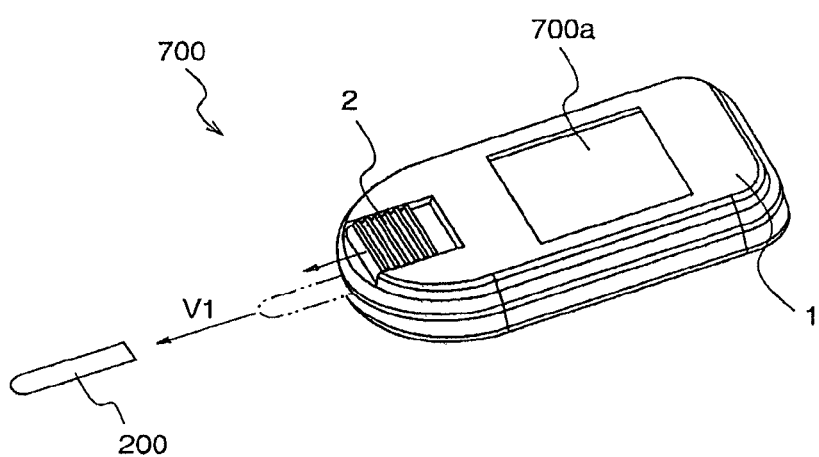
FIG. 15 is a schematic diagram of a conventional measurement device having an ejection mechanism.
Figure 16A:
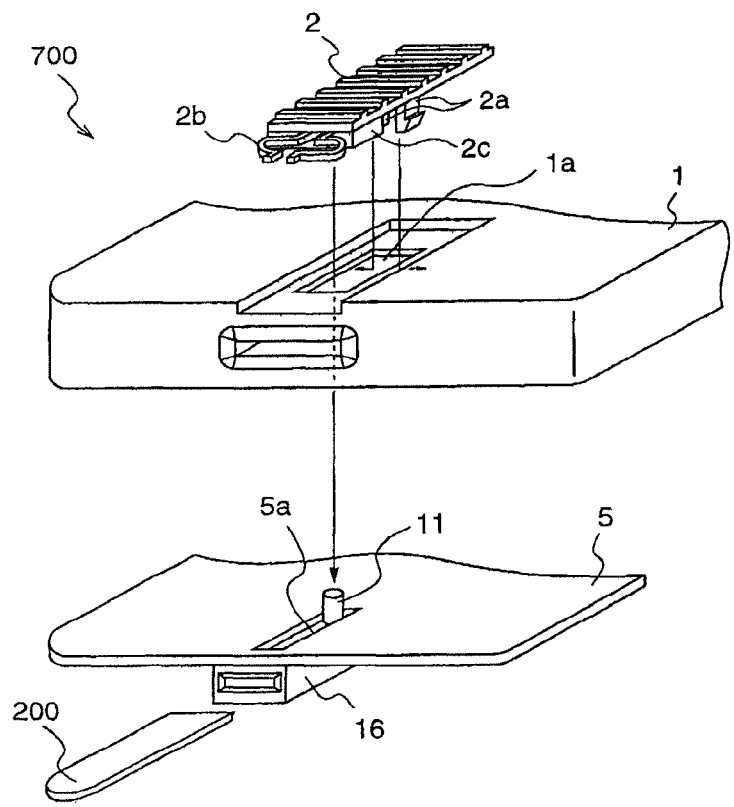
FIG. 16(a) is an exploded perspective view of the conventional measurement device having an ejection mechanism.
Figure 16B:
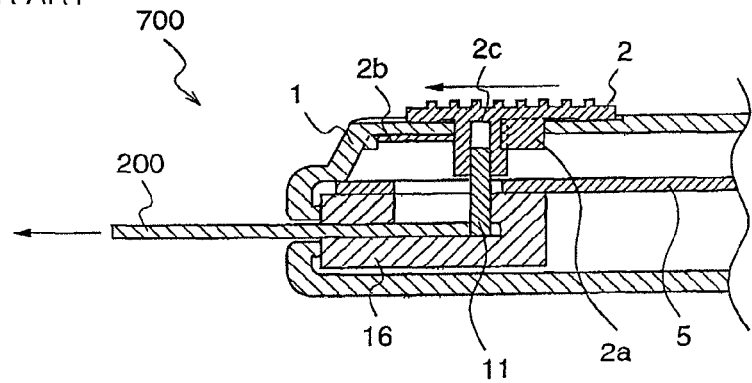
FIG. 16(b) is a cross-sectional view of the conventional measurement device having an ejection mechanism.
Figure 17A:
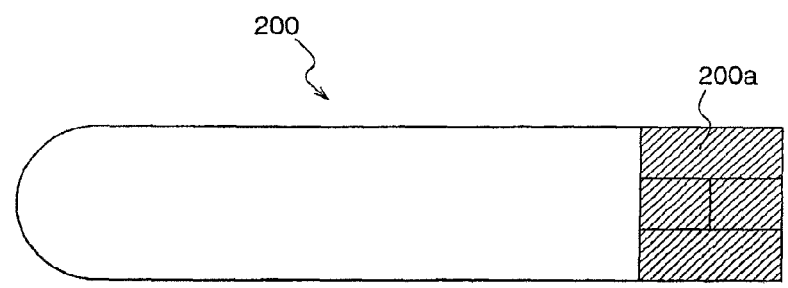
FIG. 17(a) is a diagram illustrating the configuration of a sensor.
Figure 17B:
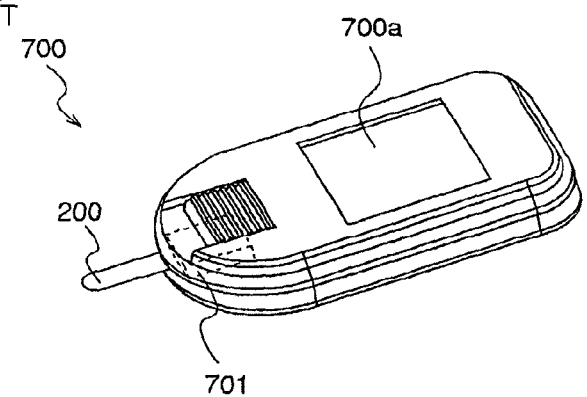
FIG. 17(b) is a schematic diagram of the conventional measurement device having an ejection mechanism.
Figure 18A:
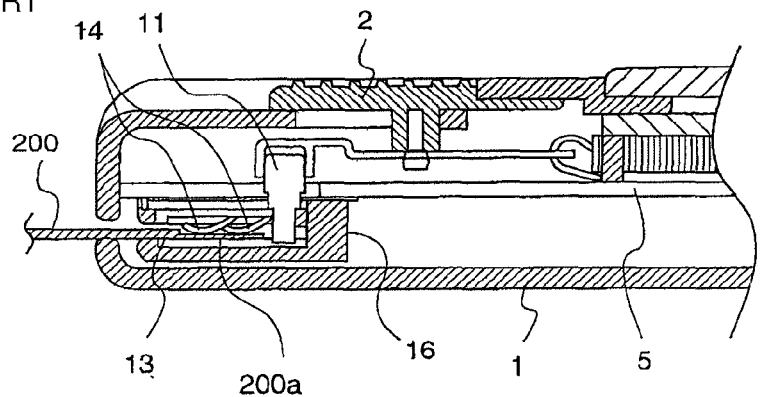
FIG. 18(a) is a specific cross-sectional view of the conventional measurement device having an ejection mechanism.
Figure 18B:
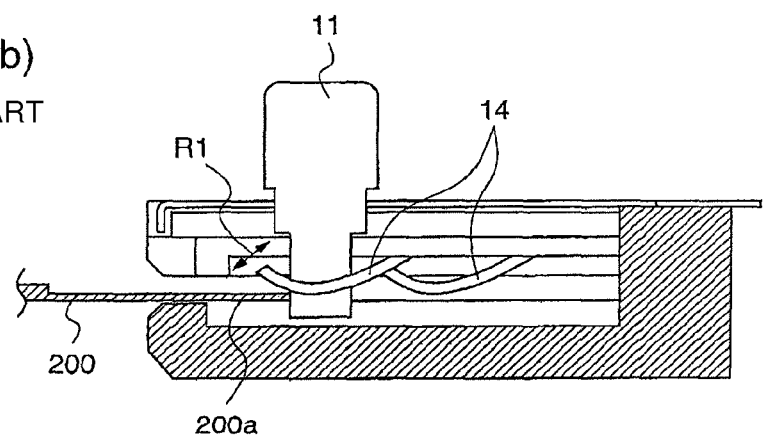
FIGS. 18(b) and 18(c) are expanded cross-sectional views of the conventional measurement device having an ejection mechanism.
Figure 18C:
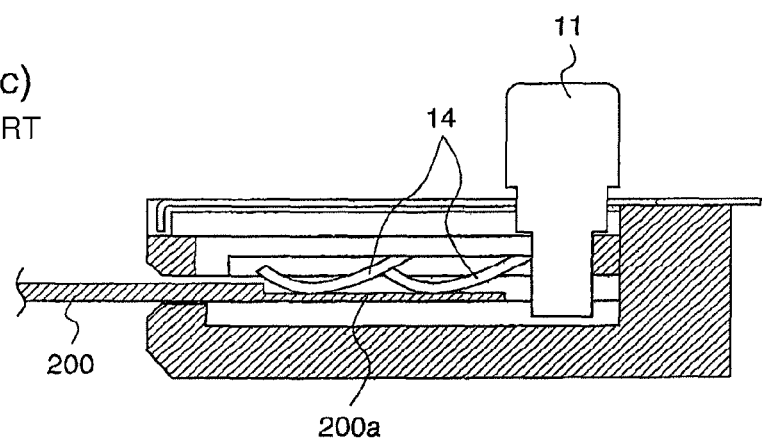
Figure 19:
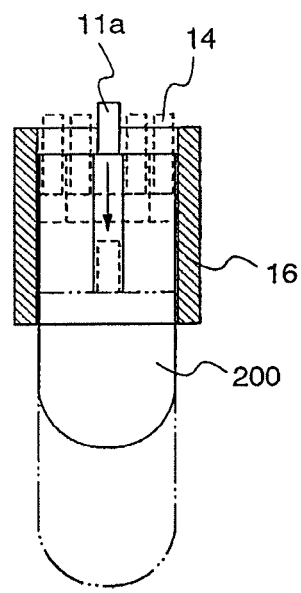
FIG. 19 is an exploded front view of a connector in the conventional measurement device having an ejection mechanism.

Next, a sensor ejection method for ejecting the sensor 200 from the measurement device will be described with reference to FIGS. 9 and 14.

The operator slides the ejection lever 2 with his finger in the direction of arrow shown in FIG. 9, i.e., in the ejection direction (step S501). A position detection switch (not shown) for detecting the position of the ejection lever 2 is changed from ON to OFF or from OFF to ON according to the position of the ejection lever 2 (step S502). When the pump 70 is electrically turned on according to the output of the position detection switch, suction or exhaust of air is carried out (step S503). This air flow reaches the flat surface of the sensor 200 through the flow channel 71, and the fifth brake part 71a moves the sensor 200 upward or downward to brake the movement of the sensor 200 in the ejection direction (step S504). Thereby, the length of jumping-out of the sensor 200 can be reduced.

After the sensor 200 is ejected from the measurement device body 1, when the operator releases the ejection lever 2, that is, cancels the force applied to the ejection lever 2 (step S505), the ejection lever 2 returns to the original position. When it is detected that the position detection switch is turned ON or OFF (step S506), the pump 70 is electrically turned OFF to halt the air suction or exhaust by the pump 70 (step S507).

By providing the brake means which applies a load due to air to the sensor through the vent hole provided on the main body side when ejecting the sensor to brake the movement of the sensor in the ejection direction, it is possible to prevent excessive jumping of the sensor 200 when it is ejected.

While only one vent hole may be provided in the center or near the center of the lateral direction of the sensor 200, this fifth embodiment is configured, although not shown in the figure, such that the flow channel 71 is branched at the front end near the sensor 200 to be connected to plural vent holes of the same dimension although not shown in the figure, and the amounts of air exhausted or sucked through the respective vent holes are made equal so as to apply a constant force to the plane surface of the sensor 200.

Further, if the amount of air to be sucked or exhausted is controlled by depressurizing or pressuring the pump 70, the movement of the sensor in the ejection direction can be braked more accurately.

While in this fifth embodiment the vent hole is orientated in the direction vertical to the plane surface of the sensor 200, it may have an appropriate angle to the surface. For example, it is found that excessive jumping of the sensor 200 when it is ejected can be prevented by slightly inclining the vent hole in the ejection direction of the sensor 200 or the direction reverse to the ejection direction during the air suction while slightly inclining the vent hole in the direction reverse to the sensor ejection direction during the air exhaust.

As described above, since the measurement device of this fifth embodiment includes the fifth brake part 71a which performs suction or exhaust of air for the sensor 200 through the vent hole provided on the main body side to brake the movement of the sensor 200 in the ejection direction during the sliding operation of pushing the sensor 200 forward by the ejection mechanism, it is possible to prevent the sensor from rapidly jumping out in an unintended direction when ejecting the sensor. Therefore, it is possible to prevent the sensor 200 from jumping out with an excessive speed the operator cannot expect, and the operator can safely discard the sensor without touching the sample attached to the sensor by mistake even when the sample contains a disease agent, and thus secondary infection of disease or the like can be avoided to enhance the reliability when the sensor is discarded.

Further, according to the measurement device of this fifth embodiment, since the ejection mechanism is operated to exert the brake force of the fifth brake part 71*a* on the sensor 200 only when ejecting the sensor, the fifth brake part 71*a* does not perform unnecessary operation except when ejecting the sensor, and it can brake the movement of the sensor in the ejection direction with the minimum operation. Further, since there is no interference by air flow when a new sensor is inserted, the sensor can be smoothly inserted in the measurement device without an excessive load on the sensor. Moreover, since the fifth brake part 71*a* provides a brake force utilizing air flow, there occurs no friction or attrition, and thereby a stable brake force can be obtained over long periods.

APPLICABILITY IN INDUSTRY

The measurement device of the present invention includes the brake means which brakes the movement of the sensor in the ejection direction after the elastic connection between the electrode terminal of the sensor and the connection terminal is released by the pushing member, and thereby the amount of jumping-out of the sensor can be controlled when ejecting the sensor. Therefore, it is possible to prevent the sensor from jumping out in the direction that is not intended by the operator, and thereby the measurement device can be applied to the field of biosensors in which prevention of blood scattering is required. Further, it can be applied to analysis devices in the environmental field as well as the medical field.

The invention claimed is:

1. A measurement device for electrochemically analyzing an analysis sample which is collected by a sensor having an electrode terminal, the measurement device comprising:
   a measurement device body;
   a sensor holding part integrated with the measurement device body, said sensor holding part being configured to hold the sensor;
   a connection terminal supported by the measurement device body, and configured to contact the electrode terminal of the sensor that is held by the sensor holding part;
   an ejection mechanism configured to eject the sensor from the sensor holding part, the ejection mechanism including an element which pushes a front side surface of the sensor while the sensor is held by the sensor holding part with the electrode terminal of the sensor contacting the connection terminal to release the contact of the electrode terminal of the sensor with the connection terminal, the front surface of the sensor being on a front side of the sensor in a direction in which the sensor is inserted into the sensor holding part; and
   a brake part provided at a portion of the measurement device body, said brake part configured to contact the sensor to brake the movement of the sensor in the ejection direction while the sensor is being ejected by the ejection mechanism,
   wherein the brake part reduces a speed with which the sensor separates from the sensor holding part.

2. The measurement device of claim 1, wherein said brake part comprises an elastic material.

3. The measurement device of claim 2, wherein said elastic material is any of a plastic, a metal, and a rubber.

4. The measurement device of claim 1, wherein said brake part is a first brake part which is provided at a position that contacts a side surface or a plane surface of the sensor.

5. The measurement device of claim 4, wherein said first brake part contacts the sensor at a sensor position where the contact of the connection terminal to the electrode terminal of the sensor is released or at a sensor position which is by a predetermined amount anterior to the sensor position where the contact is released.

6. A sensor ejection method for ejecting the sensor from the measurement device of claim 4, the method comprising:
   a first step of pushing the ejection mechanism of the measurement device;
   a second step of ejecting the sensor from the sensor holding part of the measurement device by bringing the ejection mechanism in contact with the front side surface of the sensor viewed from the measurement device body side so as to push the sensor which is held by the sensor holding part of the measurement device with the electrode terminal thereof elastically contacting the connection terminal of the measurement device to release the elastic contact of the electrode terminal of the sensor with the connection terminal of the measurement device; and
   a third step of bringing the first brake part of the measurement device in elastic contact with the side surface of the sensor to brake the movement of the sensor in the ejection direction while performing the operation of pushing the sensor by the ejection mechanism.

7. The measurement device of claim 1, wherein said brake part is a second brake part comprising a rotating body, which is provided at a position that contacts a side surface or a plane surface of the sensor.

8. A sensor ejection method of ejecting the sensor from the measurement device of claim 7, the method comprising:
   a first step of pushing the ejection mechanism of the measurement device;
   a second step of ejecting the sensor from the sensor holding part of the measurement device by bringing the ejection mechanism in contact with the front side surface of the sensor viewed from the measurement device body side so as to push the sensor which is held by the sensor holding part of the measurement device with the electrode terminal thereof elastically contacting the connection terminal of the measurement device to release the elastic contact of the electrode terminal of the sensor with the connection terminal of the measurement device; and
   a third step of bringing the second brake part of the measurement device in elastic contact with the upper and lower surfaces of the sensor and rotating the second brake part to brake the movement of the sensor in the ejection direction while performing the operation of pushing the sensor by the ejection mechanism.

9. The measurement device of claim 7, wherein said second brake part contacts the sensor at a sensor position where the contact of the connection terminal to the electrode terminal of the sensor is released or at a sensor position which is by a predetermined amount anterior to the sensor position where the contact is released.

10. The measurement device of claim 1, wherein said brake part contacts the sensor at a sensor position where the contact of the connection terminal to the electrode terminal of the sensor is released or at a sensor position which is by a predetermined amount anterior to the sensor position where the contact is released.

11. The measurement device of claim 1, wherein said brake part comprises a third brake part which contacts the sensor to brake the sensor by a solenoid when ejecting the sensor.

12. The measurement device of claim 11, wherein said third brake part comprises
- a position detection means for detecting the position of the ejection mechanism,
- a solenoid drive means for driving the solenoid according to an output of the position detection means, and
- a brake arm which is movable in conjunction with the solenoid.

13. A sensor ejection method for ejecting a sensor from the measurement device of claim 12, the method comprising:
- a first step of pushing the ejection mechanism of the measurement device;
- a second step of detecting the position of the ejection mechanism;
- a third step of driving the solenoid according to the position of the ejection mechanism; and
- a fourth step of driving the brake arm which is movable in conjunction with the solenoid to bring the third brake part of the measurement device in elastic contact with the sensor, thereby to brake the movement of the sensor in the ejection direction.

14. The measurement device of claim 1, wherein said brake part comprises a fourth brake part which contacts the sensor to brake the sensor by an eccentric cam when ejecting the sensor.

15. The measurement device of claim 14, wherein said fourth brake part comprises
- a cam drive lever which is moved in conjunction with an ejection lever provided in the ejection mechanism, and
- said eccentric cam having an engagement part that can be engaged with an end of the cam drive lever and a convex portion that contacts the sensor, and being rotatable around a shaft.

16. A sensor ejection method for ejecting a sensor from the measurement device of claim 15, the method comprising:
- a first step of pushing the ejection mechanism of the measurement device;
- a second step of driving the cam drive lever of the measurement device to bring it into contact with the eccentric cam; and
- a third step of rotating the eccentric cam around the shaft to bring the convex portion of the eccentric cam in elastic contact with the sensor, thereby to brake the movement of the sensor in the ejection direction.

17. The measurement device of claim 15, wherein the convex portion of the eccentric cam comprises an elastic material.

18. The measurement device of claim 14, wherein the elastic material is any of a plastic, a metal, and a rubber.

19. The measurement device of claim 1,
wherein the brake part is a fifth brake part provided at a portion of the measurement device body, said fifth brake part performing suction or exhaust of air to the sensor through a vent hole provided on the device body side to brake the movement of the sensor in the ejection direction while performing the operation of pushing the sensor by the ejection mechanism.

20. The measurement device of claim 19, wherein said fifth brake part comprises
- a position detection means for detecting the position of the ejection mechanism,
- a pump drive means for driving a pump which can perform suction or exhaust of air according to an output of the position detection means, and
- a flow channel which is connected to the pump at one end, and connected to the vent hole at the other end, said vent hole being provided opposed to the plane surface of the sensor.

21. The measurement device of claim 19, wherein said vent hole is provided having an appropriate angle with respect to the plane surface of the sensor.

22. The measurement device of claim 19, wherein said vent hole is provided at the upper surface or lower surface of the sensor, or at the both surfaces.

23. The measurement device of claim 19, wherein a plurality of said vent holes are provided.

24. The measurement device of claim 19, wherein said fifth brake part controls the amount of air to be sucked or exhausted by performing depressurizing or pressurizing.

25. A sensor ejection method for ejecting a sensor from the measurement device of claim 19, the method comprising:
- a first step of pushing the ejection mechanism of the measurement device;
- a second step of detecting the position of the ejection mechanism;
- a third step of driving a pump according to the position of the ejection mechanism; and
- a fourth step of performing suction or exhaust of air through a vent hole provided in the measurement device body via a flow channel connected to the pump, thereby to brake the movement of the sensor in the ejection direction.

26. A sensor ejection method for ejecting the sensor from the measurement device of claim 1, the method comprising:
- a first step of pushing the ejection mechanism of the measurement device;
- a second step of ejecting the sensor from the sensor holding part of the measurement device by bringing the ejection mechanism in contact with the front side surface of the sensor viewed from the measurement device body side so as to push the sensor which is held by the sensor holding part of the measurement device with the electrode terminal thereof elastically contacting the connection terminal of the measurement device to release the elastic contact of the electrode terminal of the sensor with the connection terminal of the measurement device; and
- a third step of bringing the brake part of the measurement device in elastic contact with the sensor to brake the movement of the sensor in the ejection direction while performing the operation of pushing the sensor by the ejection mechanism.

27. A measurement device for electrochemically analyzing an analysis sample which is collected by a sensor having an electrode terminal, the measurement device comprising:
- a measurement device body;
- a sensor holding part integrated with the measurement device body, said sensor holding part being configured to hold the sensor;
- a connection terminal supported by the measurement device body, and configured to contact the electrode terminal of the sensor that is held by the sensor holding part;
- an ejection mechanism configured to eject the sensor from the sensor holding part, the ejection mechanism including an element which pushes a front side surface of the sensor while the sensor is held by the sensor holding part with the electrode terminal of the sensor contacting the connection terminal to release the contact of the electrode terminal of the sensor with the connection terminal, the front surface of the sensor being on a front side of the sensor in a direction in which the sensor is inserted into the sensor holding part; and a brake part provided at a portion of the measurement device body, said brake part configured to contact the sensor to brake the movement of the sensor in the ejection direction while the sensor is being ejected by the ejection mechanism, wherein the brake part includes a flat surface configured to contact the sensor, and the brake part is configured to contact at least one side surface of the sensor.

28. A measurement device for electrochemically analyzing an analysis sample which is collected by a sensor having an electrode terminal, the measurement device comprising:

a measurement device body;

a sensor holding part integrated with the measurement device body, said sensor holding part being configured to hold the sensor;

a connection terminal supported by the measurement device body, and configured to contact the electrode terminal of the sensor that is held by the sensor holding part;

an ejection mechanism configured to eject the sensor from the sensor holding part in an ejection direction, the ejection mechanism including an element which pushes a front side surface of the sensor while the sensor is held by the sensor holding part with the electrode terminal of the sensor contacting the connection terminal to release the contact of the electrode terminal of the sensor with the connection terminal, the front surface of the sensor being on a front side of the sensor in a direction in which the sensor is inserted into the sensor holding part; and a brake part provided at a portion of the measurement device body, said brake part configured to contact the sensor to brake the movement of the sensor in the ejection direction while the sensor is being ejected by the ejection mechanism, wherein the brake part does not accelerate the sensor in the ejection direction.

29. A measurement device for electrochemically analyzing an analysis sample which is collected by a sensor having an electrode terminal, the measurement device comprising:

a measurement device body;

a sensor holding part integrated with the measurement device body, said sensor holding part being configured to hold the sensor;

a connection terminal supported by the measurement device body, and configured to contact the electrode terminal of the sensor that is held by the sensor holding part;

an ejection mechanism configured to eject the sensor from the sensor holding part, the ejection mechanism including an element which pushes a front side surface of the sensor while the sensor is held by the sensor holding part with the electrode terminal of the sensor contacting the connection terminal to release the contact of the electrode terminal of the sensor with the connection terminal, the front surface of the sensor being on a front side of the sensor in a direction in which the sensor is inserted into the sensor holding part; and a brake part provided at a portion of the measurement device body, said brake part configured to contact the sensor to brake the movement of the sensor in the ejection direction while the sensor is being ejected by the ejection mechanism, wherein the brake part includes a flat surface configured to contact a side surface of the sensor, the side surface of the sensor extending in a direction perpendicular to a face of the sensor which has the electrode terminal.

* * * * *